US010342559B2

(12) United States Patent
Castro et al.

(10) Patent No.: US 10,342,559 B2
(45) Date of Patent: Jul. 9, 2019

(54) ARTICULATING SURGICAL TOOLS AND TOOL SHEATHS, AND METHODS OF DEPLOYING THE SAME

(71) Applicants: Michael Salvatore Castro, Fuquay-Varina, NC (US); J. Christopher Flaherty, Auburndale, FL (US)

(72) Inventors: Michael Salvatore Castro, Fuquay-Varina, NC (US); J. Christopher Flaherty, Auburndale, FL (US)

(73) Assignee: Medrobotics Corporation, Raynham, MA (US)

( * ) Notice: Subject to any disclaimer, the term of this patent is extended or adjusted under 35 U.S.C. 154(b) by 0 days.

(21) Appl. No.: 14/944,665

(22) Filed: Nov. 18, 2015

(65) Prior Publication Data
US 2016/0066938 A1 Mar. 10, 2016

Related U.S. Application Data

(63) Continuation of application No. 14/008,775, filed as application No. PCT/US2012/032279 on Apr. 5, 2012, now Pat. No. 9,962,179.
(Continued)

(51) Int. Cl.
*A61B 17/00* (2006.01)
*A61B 17/29* (2006.01)
(Continued)

(52) U.S. Cl.
CPC ........ *A61B 17/29* (2013.01); *A61B 17/00234* (2013.01); *A61B 19/22* (2013.01);
(Continued)

(58) Field of Classification Search
CPC ..................... A61B 17/29; A61B 2017/00296
See application file for complete search history.

(56) References Cited

U.S. PATENT DOCUMENTS 2,513,027 A  6/1950 Kruczek
5,251,611 A  10/1993 Zehel et al.
(Continued)

FOREIGN PATENT DOCUMENTS

CN  101106935  1/2008
EP  0653922  11/2005
(Continued)

OTHER PUBLICATIONS

"Articulating Surgical Tools and Tool Sheaths, and Methods of Deploying the Same", Specification, Drawings, Claims and Prosecution History, of U.S. Appl. No. 14/008,775, filed Sep. 30, 2013 by Michael S. Castro, et al., which is stored in the U.S. Patent and Trademark Office (USPTO).
(Continued)

*Primary Examiner* — Carl H Layno
*Assistant Examiner* — Dacheng Xie
(74) *Attorney, Agent, or Firm* — Onello & Mello, LLP.

(57) ABSTRACT

A system for performing a medical procedure includes an articulating probe including inner and outer sleeves, and a surgical tool including a functional element positioned at a distal end of a tool shaft, the tool shaft having an articulation region. The articulating probe and the surgical tool are independently controllable.

13 Claims, 14 Drawing Sheets

Related U.S. Application Data

(60) Provisional application No. 61/472,344, filed on Apr. 6, 2011.

(51) Int. Cl.
*A61B 19/00* (2006.01)
*A61B 17/34* (2006.01)
*A61B 18/00* (2006.01)
*A61B 1/005* (2006.01)
*A61B 34/00* (2016.01)

(52) U.S. Cl.
CPC .......... *A61B 1/0055* (2013.01); *A61B 34/70* (2016.02); *A61B 2017/00296* (2013.01); *A61B 2017/00314* (2013.01); *A61B 2017/00323* (2013.01); *A61B 2017/00535* (2013.01); *A61B 2017/2905* (2013.01); *A61B 2017/2906* (2013.01); *A61B 2017/2908* (2013.01); *A61B 2017/347* (2013.01); *A61B 2017/3445* (2013.01); *A61B 2018/00577* (2013.01); *A61B 2019/2242* (2013.01)

(56) References Cited

U.S. PATENT DOCUMENTS

| | | |
|---|---|---|
| 5,254,130 A | 10/1993 | Poncet et al. |
| 5,273,026 A | 12/1993 | Wilk |
| 5,405,344 A | 4/1995 | Williamson et al. |
| 5,435,286 A | 7/1995 | Carroll, III et al. |
| 5,454,827 A | 10/1995 | Aust et al. |
| 5,507,296 A | 4/1996 | Bales et al. |
| 5,520,678 A | 5/1996 | Heckele et al. |
| 5,524,180 A | 6/1996 | Wang et al. |
| 5,624,381 A | 4/1997 | Kieturakis |
| 5,643,294 A | 7/1997 | Tovey et al. |
| 5,665,105 A | 9/1997 | Furnish et al. |
| 5,702,408 A | 12/1997 | Wales et al. |
| 5,759,151 A | 6/1998 | Sturges |
| 5,815,640 A | 9/1998 | Wang et al. |
| 5,841,950 A | 11/1998 | Wang et al. |
| 5,907,664 A | 5/1999 | Wang et al. |
| 5,916,146 A | 6/1999 | Allotta et al. |
| 5,916,147 A | 6/1999 | Boury |
| 5,938,678 A | 8/1999 | Zirps et al. |
| 5,987,757 A | 11/1999 | Schmidt et al. |
| 6,080,181 A | 6/2000 | Jensen et al. |
| 6,132,368 A | 10/2000 | Cooper |
| 6,210,416 B1 | 4/2001 | Chu et al. |
| 6,346,072 B1 | 2/2002 | Cooper |
| 6,666,854 B1 | 12/2003 | Lange |
| 6,837,846 B2 | 1/2005 | Jaffe et al. |
| 6,837,847 B2 | 1/2005 | Ewers et al. |
| 7,090,637 B2 | 8/2006 | Danitz |
| 7,147,650 B2 | 12/2006 | Lee |
| 7,250,028 B2 | 7/2007 | Julian et al. |
| 7,338,513 B2 | 3/2008 | Lee et al. |
| 7,357,774 B2 | 4/2008 | Cooper |
| 7,364,582 B2 | 4/2008 | Lee |
| 7,381,018 B2 | 6/2008 | Zepic et al. |
| 7,410,483 B2 | 8/2008 | Danitz et al. |
| D583,051 S | 12/2008 | Lee et al. |
| 7,553,275 B2 | 6/2009 | Padget et al. |
| 7,575,548 B2 | 8/2009 | Takemoto et al. |
| 7,615,066 B2 | 11/2009 | Danitz et al. |
| 7,615,067 B2 | 11/2009 | Lee et al. |
| 7,648,519 B2 | 1/2010 | Lee et al. |
| 7,682,307 B2 | 3/2010 | Danitz et al. |
| 7,686,826 B2 | 3/2010 | Lee et al. |
| 7,708,758 B2 | 5/2010 | Lee et al. |
| 7,789,875 B2 | 9/2010 | Brock et al. |
| 7,819,885 B2 | 10/2010 | Cooper |
| 7,828,808 B2 | 11/2010 | Hinman et al. |
| 7,842,028 B2 | 11/2010 | Lee |
| 7,850,642 B2 | 12/2010 | Moll et al. |
| 7,854,109 B2 | 12/2010 | Zubiate et al. |
| 7,854,738 B2 | 12/2010 | Lee et al. |
| D631,155 S | 1/2011 | Peine et al. |
| 7,867,241 B2 | 1/2011 | Brock et al. |
| 7,946,546 B2 | 5/2011 | Zubiate et al. |
| D640,789 S | 6/2011 | Peine et al. |
| 8,029,531 B2 | 10/2011 | Lee et al. |
| 8,083,765 B2 | 12/2011 | Lee et al. |
| 8,100,031 B2 | 1/2012 | Zubiate et al. |
| 8,105,350 B2 | 1/2012 | Lee et al. |
| 8,114,118 B2 | 2/2012 | Knodel et al. |
| 8,177,794 B2 | 5/2012 | Cabrera et al. |
| 8,182,417 B2 | 5/2012 | Danitz |
| 8,192,422 B2 | 6/2012 | Zubiate et al. |
| 8,221,450 B2 | 7/2012 | Lee et al. |
| 8,246,637 B2 | 8/2012 | Viola et al. |
| 8,257,386 B2 | 9/2012 | Lee et al. |
| 8,292,905 B2 | 10/2012 | Taylor et al. |
| 8,292,906 B2 | 10/2012 | Taylor et al. |
| 8,337,515 B2 | 12/2012 | Viola et al. |
| 8,372,090 B2 | 2/2013 | Wingardner et al. |
| 8,409,175 B2 | 4/2013 | Lee et al. |
| 8,409,245 B2 | 4/2013 | Lee |
| 8,459,138 B2 | 6/2013 | Zubiate et al. |
| 8,460,275 B2 | 6/2013 | Taylor et al. |
| 8,496,674 B2 | 7/2013 | Cabrera et al. |
| 8,506,581 B2 | 8/2013 | Wingardner, III et al. |
| 8,636,752 B2 | 1/2014 | Cabrera et al. |
| 8,709,037 B2 | 4/2014 | Lee et al. |
| 8,747,424 B2 | 6/2014 | Taylor et al. |
| 8,926,597 B2 | 1/2015 | Lee |
| 8,968,342 B2 | 3/2015 | Wingardner, III et al. |
| 9,113,860 B2 | 8/2015 | Viola et al. |
| 9,168,050 B1 | 10/2015 | Peine et al. |
| 9,271,723 B2 | 3/2016 | Taylor et al. |
| 9,345,462 B2 | 5/2016 | Weitzner et al. |
| 9,427,256 B2 | 8/2016 | Lee |
| 2002/0091374 A1 | 7/2002 | Cooper |
| 2003/0158463 A1 | 8/2003 | Julian et al. |
| 2004/0138529 A1* | 7/2004 | Wiltshire ............ A61B 1/0055 600/144 |
| 2004/0193146 A1 | 9/2004 | Lee et al. |
| 2004/0236316 A1 | 11/2004 | Danitz |
| 2005/0021050 A1 | 1/2005 | Cooper |
| 2005/0107667 A1 | 5/2005 | Danitz et al. |
| 2005/0125027 A1 | 6/2005 | Knodel et al. |
| 2005/0165429 A1 | 7/2005 | Douglas et al. |
| 2005/0222495 A1 | 10/2005 | Okada et al. |
| 2005/0251112 A1 | 11/2005 | Danitz et al. |
| 2005/0267335 A1 | 12/2005 | Okada et al. |
| 2005/0273084 A1* | 12/2005 | Hinman ................ A61B 1/008 606/1 |
| 2006/0069304 A1 | 3/2006 | Takemoto et al. |
| 2006/0074407 A1 | 4/2006 | Padget et al. |
| 2006/0094931 A1 | 5/2006 | Danitz et al. |
| 2006/0111210 A1 | 5/2006 | Hinman |
| 2006/0111616 A1 | 5/2006 | Danitz |
| 2007/0003385 A1 | 1/2007 | Zepic et al. |
| 2007/0093790 A1 | 4/2007 | Downey et al. |
| 2007/0163100 A1 | 7/2007 | Schmidt et al. |
| 2007/0221700 A1 | 9/2007 | Ortiz et al. |
| 2007/0250110 A1 | 10/2007 | Lu et al. |
| 2007/0270640 A1 | 11/2007 | Dimitriou et al. |
| 2007/0276180 A1 | 11/2007 | Greenburg et al. |
| 2007/0276430 A1 | 11/2007 | Lee et al. |
| 2008/0064921 A1 | 3/2008 | Larkin et al. |
| 2008/0147091 A1 | 6/2008 | Cooper |
| 2008/0188868 A1 | 8/2008 | Weitzner et al. |
| 2008/0243106 A1* | 10/2008 | Coe ................ A61B 17/00234 606/1 |
| 2008/0245173 A1 | 10/2008 | Schwerin et al. |
| 2008/0255420 A1 | 10/2008 | Lee et al. |
| 2008/0287963 A1* | 11/2008 | Rogers ............ A61B 1/00039 606/130 |
| 2009/0143639 A1 | 6/2009 | Stark |
| 2009/0171151 A1 | 7/2009 | Choset et al. |
| 2009/0259141 A1 | 10/2009 | Ewers et al. |
| 2010/0010512 A1 | 1/2010 | Taylor et al. |
| 2010/0179540 A1 | 7/2010 | Marczyk et al. |

(56) References Cited

U.S. PATENT DOCUMENTS

| | | |
|---|---|---|
| 2010/0228270 A1 | 9/2010 | Bogart et al. |
| 2011/0021871 A1 | 1/2011 | Berkelaar |
| 2011/0028790 A1 | 2/2011 | Farr et al. |
| 2011/0028990 A1 | 2/2011 | Cooper |
| 2011/0066161 A1 | 3/2011 | Cooper |
| 2011/0152613 A1 | 6/2011 | Zubiate et al. |
| 2011/0184241 A1 | 7/2011 | Zubiate et al. |
| 2011/0198386 A1 | 8/2011 | Viola |
| 2011/0238108 A1 | 9/2011 | Peine et al. |
| 2011/0313243 A1 | 12/2011 | Zubiate et al. |
| 2012/0078248 A1 | 3/2012 | Worrell et al. |
| 2012/0109186 A1 | 5/2012 | Parrott et al. |
| 2012/0138834 A1 | 6/2012 | Tortel et al. |
| 2012/0240201 A1 | 9/2012 | Ramaswamy et al. |
| 2012/0253324 A1 | 10/2012 | Lee et al. |
| 2012/0253326 A1 | 10/2012 | Kleyman |
| 2012/0265220 A1 | 10/2012 | Menn |
| 2013/0023915 A1 | 1/2013 | Mueller |
| 2014/0336675 A1 | 11/2014 | Menn |
| 2016/0354114 A1 | 12/2016 | Lee |
| 2017/0196546 A1 | 7/2017 | Lee |

FOREIGN PATENT DOCUMENTS

| | | |
|---|---|---|
| EP | 1015068 | 9/2011 |
| JP | 57123101 | 7/1982 |
| JP | 2000037390 | 2/2000 |
| JP | 2002090656 | 3/2002 |
| JP | 2002330928 | 11/2002 |
| JP | 2002090656 | 3/2003 |
| JP | 2005287963 | 10/2005 |
| JP | 2005334237 | 12/2005 |
| JP | 2006087687 | 4/2006 |
| JP | 2007502198 | 2/2007 |
| JP | 2009538186 | 11/2009 |
| JP | 2009539573 | 11/2009 |
| JP | 2010505519 | 2/2010 |
| JP | 2010511440 | 4/2010 |
| WO | 2008045386 | 4/2008 |
| WO | 2011127137 | 10/2011 |
| WO | 2012015659 | 2/2012 |

OTHER PUBLICATIONS

Office Action dated Jul. 30, 2015 from related family application EP 12768046.0.
Extended European Search Report dated Aug. 20, 2014, issued in corresponding International Patent Application No. PCT/US2012/032279.
International Search Report dated Nov. 8, 2013 issued in corresponding International Application No. PCT/US2013/043858.
International Search Report dated Sep. 5, 2015 issued in corresponding PCT/US2014/038701.
International Search Report and the Written Opinion dated Oct. 12, 2012, issued in corresponding International Patent Application No. PCT/US2012/032279.
"Articulating Surgical Tools and Tool Sheaths, and Methods of Deploying the Same", Specification, Drawings, Claims and Prosecution History, of PCT Application No. PCT/US12/32279 filed Apr. 5, 2012 by Michael S. Castro, et al., which is stored in the U.S. Patent and Trademark Office (USPTO).
Office Action dated Aug. 24, 2015 issued in corresponding Israeli Application No. 228734 with English summary.
Office Action dated Jun. 30, 2015 issued in corresponding Chinese Application No. 20128002740.6 with English summary.
Office Action dated Mar. 2, 2016 issued in corresponding Chinese Application No. 2012800227470.6 with English summary.
Examination Report dated Feb. 9, 2016 issued in corresponding Australian Application No. 2012240201.
Office Action dated Mar. 8, 2016 issued in corresponding Japanese Application No. 2014-503973 with English language summary.
Office Action dated Mar. 30, 2016 issued in related European Application No. 12768046.0.
Australian Office Action dated Sep. 22, 2017 issued in corresponding Australian application No. 2017200905.
Israel Office Action dated Nov. 29, 2017 issued in corresponding Israel Application No. 228734, with English language summary.
Chinese Office Action dated Dec. 1, 2017 issued in corresponding Chinese Application No. 100081 with English language summary.
Chinese Office Action dated May 25, 2017 issued in corresponding Chinese Application No. 201280027470.6, with English language summary.
Japanese Office Action dated Aug. 29, 2017 issued in corresponding Japanese Application No. 2014-503973, with English language machine translation.
Chinese Office Action dated Nov. 10, 2016 issued in corresponding Chinese Application No. 201280027470.6.
Israel Office Action dated Nov. 16, 2016 issued in corresponding Israel Application No. 228734.
European Office Action dated Nov. 28, 2016 issued in corresponding European Application No. 12768046.0.
Australian Examination Report dated Dec. 14, 2016 issued in corresponding Australian Application No. 2012240201.
Japanese Office Action dated Dec. 20, 2016 issued in corresponding Japanese Application No. 2014503973.
Summons to Attend Oral Proceedings dated Oct. 4, 2017 issued in corresponding European Application No. 12768046.0.
Japanese Office Action dated Mar. 6, 2018 issued in corresponding Japanese Application No. 2014-503973, with English language translation.
Mexican Office Action dated Nov. 14, 2018 issued in corresponding Mexican Application No. MX/a/2013/011564, with English summary.
Japanese Office Action dated Dec. 4, 2018 issued in corresponding Japanese Application No. 2018-000117, with machine translation to English.
Canadian Office Action dated Apr. 11, 2018 issued in corresponding Canadian Application No. 2831898.
Mexican Office Action dated Apr. 13, 2018 issued in corresponding Mexican Application No. MX/a/2013/011564, with English translation.
Chinese Office Action dated May 30, 2018 issued in corresponding Chinese Application No. 201280027470.6.
Israel Office Action dated Jun. 26, 2018 issued in corresponding Israel Application No. 228734.
United States Office Action dated Jun. 13, 2018 issued in corresponding U.S. Appl. No. 14/945,685.
Korean Office Action dated Oct. 12, 2018 issued in corresponding Korean Application No. 10-2013-7029418, with English translation.
Australian Office Action dated Mar. 6, 2019 issued in corresponding Australian Application No. 2018206688.
Canadian Office Action dated Feb. 25, 2019 issued in corresponding Canadian Application No. 2831898.
U.S. Final Office Action dated Dec. 27, 2018 issued in related U.S. Appl. No. 14/945,685.
Extended European Search Report dated Apr. 26, 2019 issued in corresponding European Application No. 18200760.9.

* cited by examiner

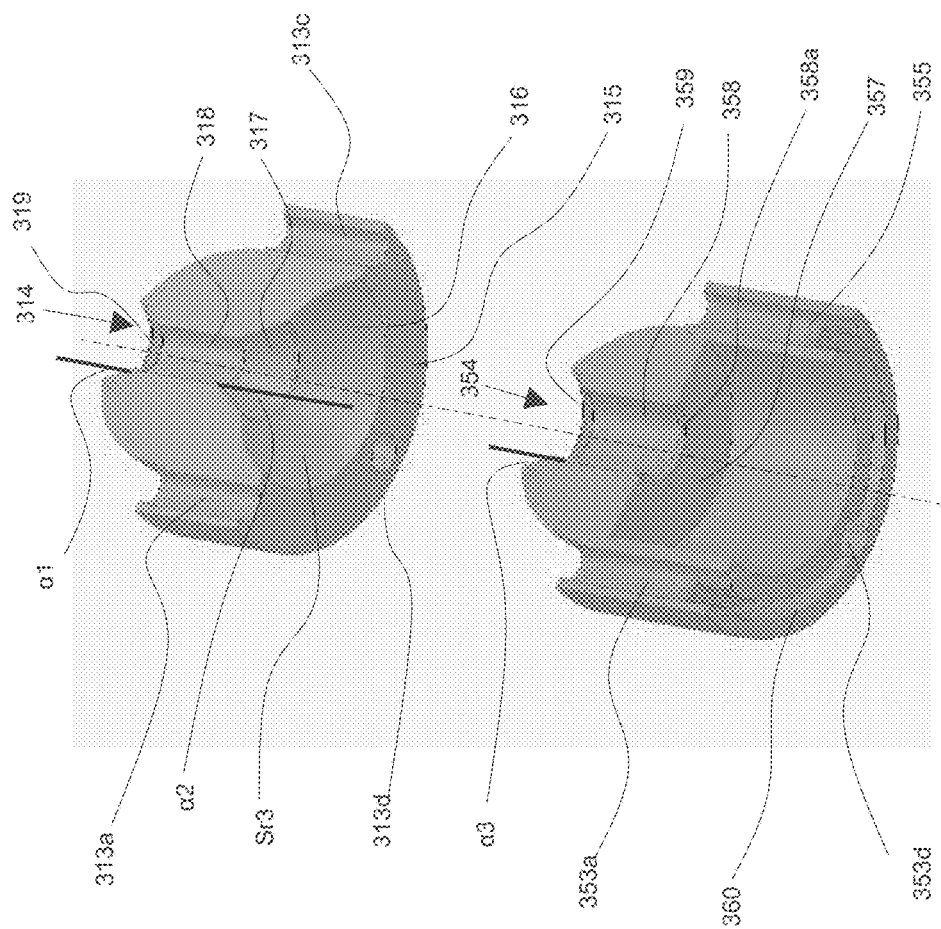

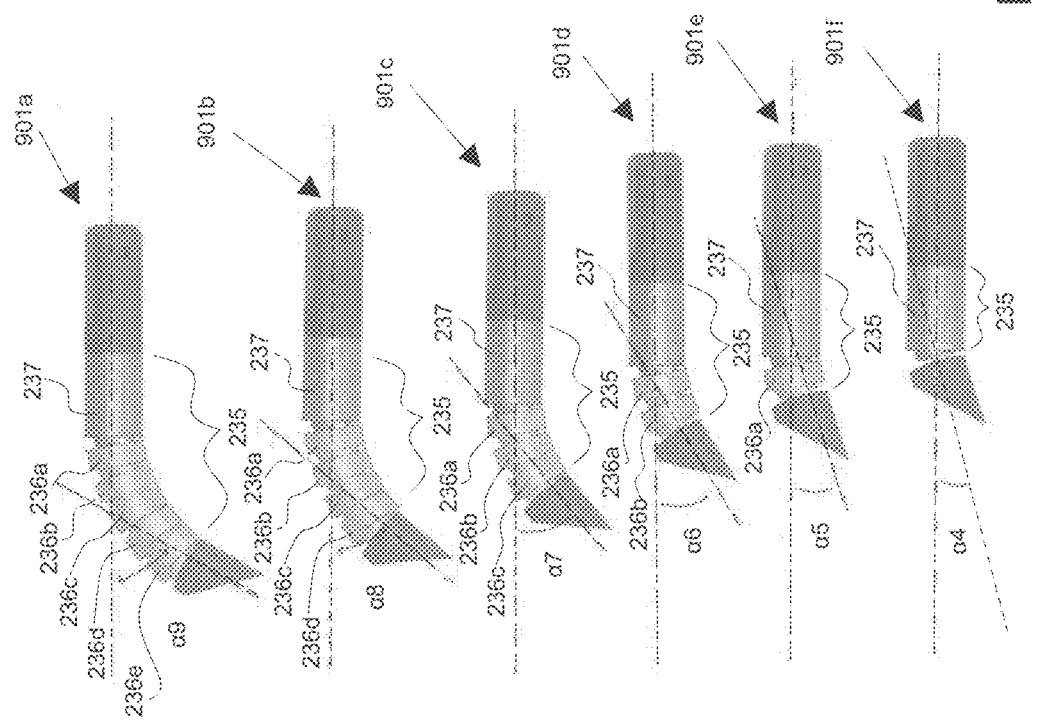

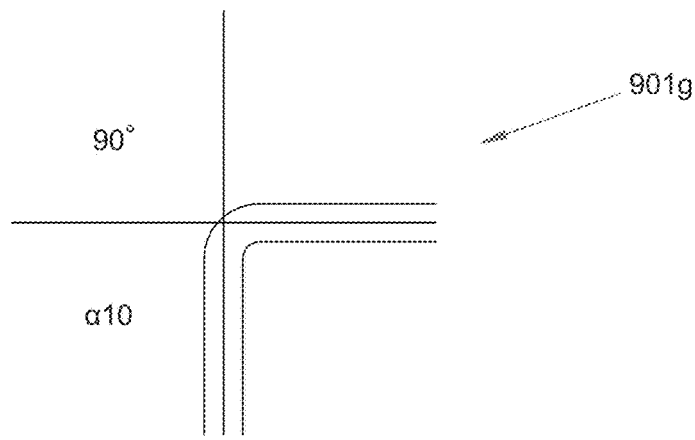
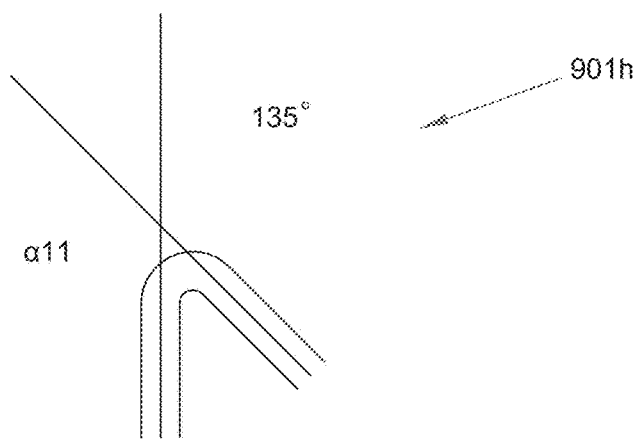
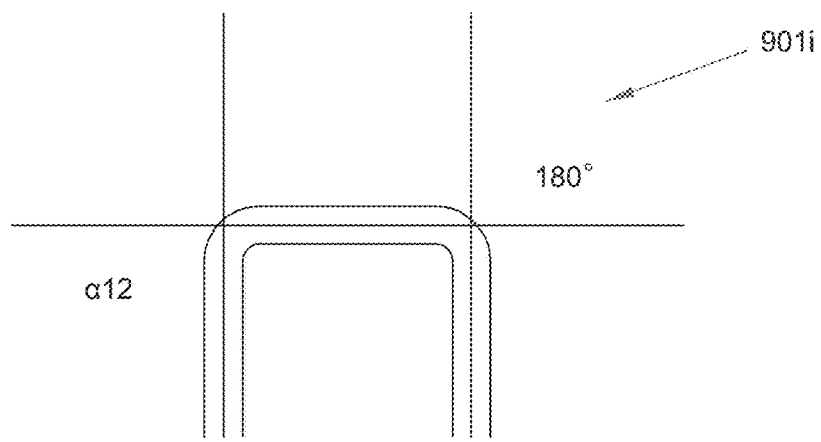
FIG 5B

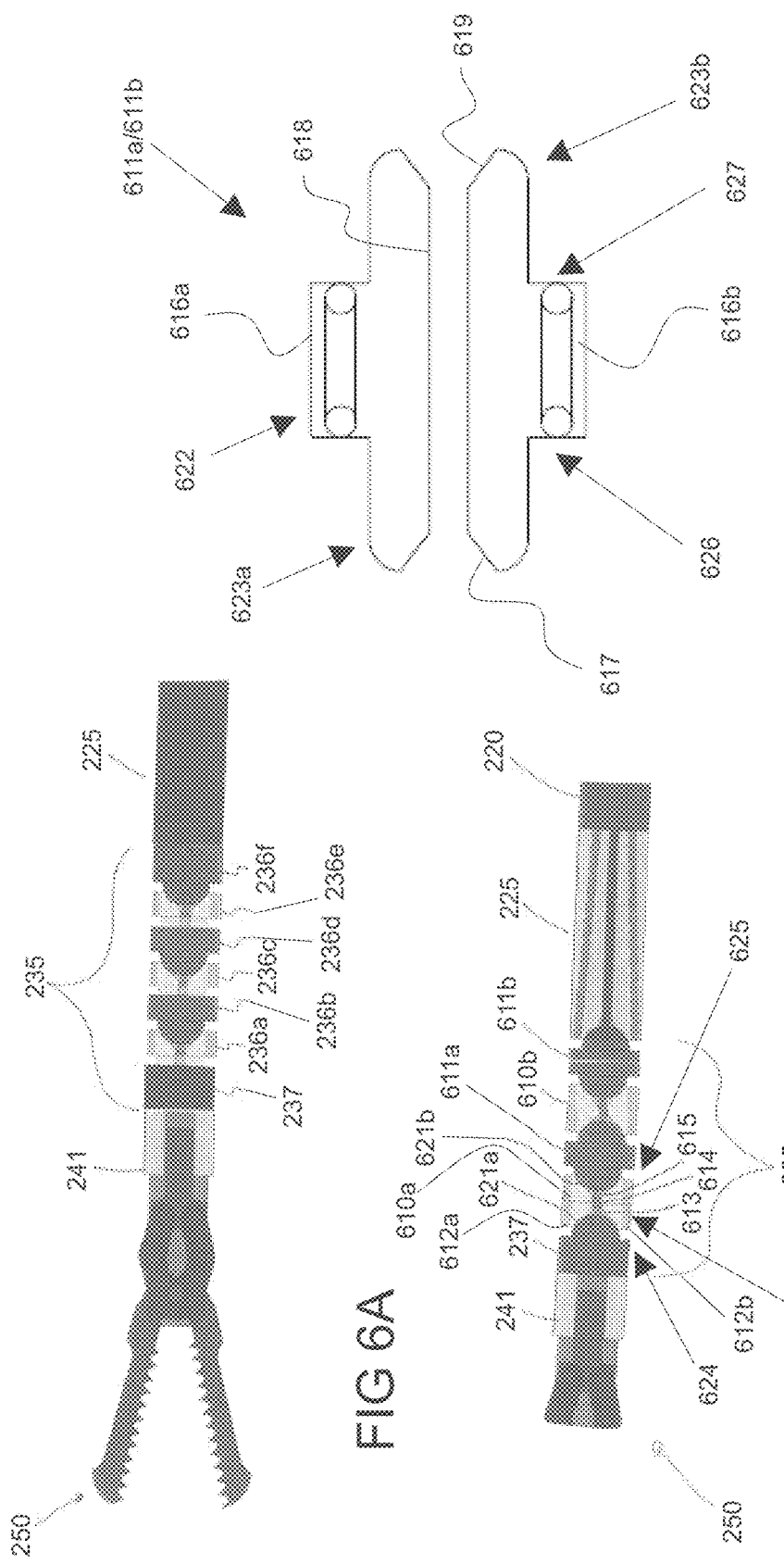

ARTICULATING SURGICAL TOOLS AND TOOL SHEATHS, AND METHODS OF DEPLOYING THE SAME

RELATED APPLICATIONS

This Application is a continuation application of U.S. Ser. No. 14/008,775, issued as U.S. Pat. No. 9,962,179, which claims the benefit of PCT Application PCT/US12/32279, filed Apr. 5, 2012, which claims the benefit of U.S. Provisional Patent Application No. 61/472,344, filed Apr. 6, 2011, the content of which is incorporated herein by reference in its entirety.

This application is related to PCT Application No PCT/US2011/060214, filed Nov. 10, 2011, the content of which is incorporated herein by reference in its entirety.

This application is related to U.S. Provisional Application No. 61/412,733, filed Nov. 11, 2010, the content of which is incorporated herein by reference in its entirety.

This application is related to U.S. Provisional Application No. 61/534,032, filed Sep. 13, 2011, the content of which is incorporated herein by reference in its entirety.

This application is related to U.S. Provisional Application No. 61/492,578, filed Jun. 2, 2011, the content of which is incorporated herein by reference in its entirety.

This application is related to U.S. Provisional Application No. 61/406,032, filed Oct. 22, 2010, the content of which is incorporated herein by reference in its entirety.

This application is related to PCT Application No PCT/US2011/057282, filed Oct. 21, 2011, the content of which is incorporated herein by reference in its entirety.

This application is related to U.S. Provisional Application No. 61/368,257, filed Jul. 28, 2010, the content of which is incorporated herein by reference in its entirety.

This application is related to PCT Application No PCT/US2011/044811, filed Jul. 21, 2011, the content of which is incorporated herein by reference in its entirety.

This application is related to U.S. Provisional Application No. 61/578,582, filed Dec. 21, 2011, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

TECHNICAL FIELD

The present inventive concepts generally relate to the field of surgical tools, and more particularly, to articulating surgical tools and tool sheaths, methods of deploying articulating surgical tools and tool sheaths, and methods of forming the same.

BACKGROUND

As less invasive medical techniques and procedures become more widespread, medical professionals, such as surgeons, may require articulating surgical tools to perform such less invasive medical techniques and procedures from outside the human body. However, conventional articulating surgical tools, such as endoscopes and other types of tools, may have limited turning radii and reduced payload stability at high articulation ranges.

SUMMARY

Embodiments of the present inventive concepts may be directed to articulating surgical tools and tool sheaths that have extended turning radii and increased payload stability at high articulation ranges.

In one aspect, a system for performing a medical procedure comprises: an articulating probe including inner and outer sleeves; and a surgical tool including a functional element positioned at a distal end of a tool shaft, the tool shaft having an articulation region, wherein the articulating probe and the surgical tool are independently controllable.

In some embodiments, the articulating probe is constructed and arranged to be controlled via a human interface device. The human interface device may include one or more selected from the group consisting of: a haptic controller, a joystick, a track ball, a mouse and an electromechanical device.

In some embodiments, the surgical tool is constructed and arranged to be controlled via a surgical tool handle. The surgical tool handle may include one selected from the group consisting of: scissor handles, a palm-held grip, a thumb/index/middle finger grip and a pistol grip.

In some embodiments, the articulating probe further includes at least one working channel having an opening at a working surface of the articulating probe, the working surface being at a distal end of the articulating probe. A portion of the tool shaft may be positioned within the at least one working channel. The functional element of the surgical tool may extend outwardly from the opening. The functional element may be constructed and arranged to articulate with respect to the working surface of the articulating probe. The functional element may be constructed and arranged to articulate with respect to an axis of extension of the tool shaft. The functional element may be constructed and arranged to articulate between 0° and 90° with respect to the working surface of the articulating probe. The functional element may be constructed and arranged to articulate between 0° and 135° with respect to the working surface of the articulating probe. The functional element may be constructed and arranged to articulate between 0° and 180° with respect to the working surface of the articulating probe.

In some embodiments, the outer sleeve of the articulating probe includes at least one side port. The at least one side port may include a side port lock. The side port lock may include a pneumatic lock. The pneumatic lock may include a solenoid. The pneumatic lock may include an expandable pouch. The side port lock may include a hydraulic lock. The hydraulic lock may include a solenoid. The hydraulic lock may include an expandable pouch or balloon. The side port lock may include an electrically activated lock. The electrically activated lock may include a solenoid. The electrically activated lock may include a piezoelectric actuator. The side port lock may be positioned within the at least one side port. The side port lock may be constructed and arranged to secure a tool shaft that passes through the at least one side port in a locked mode. The side port lock may be constructed and arranged to allow a tool shaft to pass through the at least one side port in an unlocked mode.

In some embodiments, the outer sleeve of the articulating probe includes at least one side port. A portion of the tool shaft may pass through the at least one side port. The side port may guide the tool shaft along an outer surface of the outer sleeve. The functional element of the surgical tool may extend outwardly from a working surface of the articulating probe, the working surface being at a distal end of the articulating probe. The functional element may be constructed and arranged to articulate with respect to the working surface of the articulating probe. The functional element may be constructed and arranged to articulate with respect to an axis of extension of the tool shaft. The functional element may be constructed and arranged to articulate between 0° and 90° with respect to the working surface of the articulating probe. The functional element may be constructed and arranged to articulate between 0° and 135° with respect to the working surface of the articulating probe. The functional element may be constructed and arranged to articulate between 0° and 180° with respect to the working surface of the articulating probe.

In some embodiments, each of the inner and outer sleeves of the articulating probe includes a plurality of probe links.

In some embodiments, the inner sleeve and the outer sleeve of the articulating probe are independently controllable. Each of the inner and outer sleeves of the articulating probe may be configured in one of a limp mode and a rigid mode.

In some embodiments, the articulating probe includes at least one steering cable. The at least one steering cable may terminate at a region proximal to a distal end of the articulating probe.

In some embodiments, the functional element includes one or more selected from the group consisting of: a grasper, a claw, a cutter, a knife, an ablator, a cauterizer, a drug delivery apparatus, a radiation source, an EKG electrode, a pressure sensor, a blood sensor, a camera, a magnet, a heating element and a cryogenic element.

In some embodiments, the functional element includes a first tool sheath cavity and the tool shaft includes a second tool sheath cavity. The surgical tool may be constructed and arranged to provide a cavity path for entry of a second surgical tool. The first tool sheath cavity and second tool sheath cavity may be coupled to form the cavity path. A region of the cavity path may correspond to the articulation region of the tool shaft.

In some embodiments, the surgical tool includes a locking device constructed and arranged to lock an articulated position of the functional element.

In some embodiments, the surgical tool includes a locking device constructed and arranged to lock an operational mode of the functional element.

In some embodiments, the functional element includes a grasper. The grasper may be constructed and arranged to apply a grasping force of approximately 1 $lb_F$. The grasper may be constructed and arranged to apply a grasping force of approximately 1 $lb_F$ when the articulation region is positioned in a fully articulated state.

In some embodiments, the system is constructed and arranged to perform a transoral robotic surgery procedure.

In some embodiments, the articulation region of the tool shaft includes at least two segment links. One segment link of the at least two segment links may be unitary. Each segment link of the at least two segment links may be unitary. A first segment link of the at least two segment links may be coupled to a first shaft portion of the tool shaft, and a second segment link of the at least two segment links may be coupled to a second shaft portion of the tool shaft. The functional element may be coupled to the second shaft portion. A first segment link of the at least two segment links may be coupled to a first shaft portion of the tool shaft, and a second segment link of the at least two segment links may be coupled to the functional element. The articulation region of the tool shaft may further include one or more third segment links coupled between the first segment link and the second segment link.

The first segment link may include a body having a first portion and a second portion, wherein the second portion includes a semi-spherical body portion. The first segment link may include a body having a first portion and a second portion, wherein the second portion includes a convex body portion. The convex body portion may be a semi-spherical body portion. The convex body portion may be a semi-ellipsoidal body portion. The first portion may include a cylindrical body portion. The semi-spherical body portion of the first segment link may mate with a semi-spherical cavity portion of the first shaft portion. The semi-spherical body portion of the first segment link may mate with a concave cavity portion of the first shaft portion. The concave cavity portion may be a semi-spherical cavity portion. The concave cavity portion may be a semi-ellipsoidal cavity portion.

The first segment link may include at least one articulation cable channel. The at least one articulation cable channel may include a first opening in an upper surface of the first portion and a second opening in a bottom surface of the first portion. The first portion may include a cylindrical body portion. The at least one articulation cable channel may comprise first through fourth articulation cable channels that may be spaced 90° apart around the circumference or perimeter of the first portion. The at least one articulation cable channel may comprise first through fourth articulation cable channels that may be positioned 90° apart from one another along a common radial path relative to a center axis of the first portion. The first portion may include a cylindrical body portion.

The first segment may include an actuation cable channel. The actuation cable channel may include a first opening at a diametric midpoint of the semi-spherical body portion of the first segment and a second opening at a diametric midpoint of the first portion of the first segment. The first portion may include a cylindrical body portion. The actuation cable channel may include an upper taper joined at the first opening that conforms the first opening with a cylindrical cavity of the body of the first segment. The cylindrical cavity may join a lower taper of the body of the first segment. The lower taper may conform the cylindrical cavity with a semi-spherical cavity of the body of the first segment. The second segment link may include a body having a first portion and a second portion, wherein the second portion includes a semi-spherical body portion.

The second segment link may include a body having a first portion and a second portion, wherein the second portion includes a convex body portion. The convex body portion may be a semi-spherical body portion. The convex body portion may be a semi-ellipsoidal body portion. The first portion may include a cylindrical body portion. The semi-spherical body portion of the second segment link may mate with a semi-spherical cavity portion of the first segment link. The semi-spherical body portion of the second segment link may mate with a concave cavity portion of the first segment link. The concave cavity portion may be a semi-spherical cavity portion. The concave cavity portion may be a semi-ellipsoidal cavity portion. At least two articulation cable channels of the first segment link may be aligned with at least two articulation cable channels of the second segment link. Each articulation cable channel of the first segment link may be aligned with each articulation cable channel of the second segment link.

The body of the second segment link may include at least one articulation cable channel. The at least one articulation cable channel may include a first opening in an upper surface of the first portion and a second opening in a bottom surface of the first portion. The first portion may include a cylindrical body portion. The at least one articulation cable channel may comprise first through fourth articulation cable channels that are spaced 90° apart around the circumference or perimeter of the first portion. The at least one articulation cable channel may comprise first through fourth articulation cable channels that positioned 90° apart from one another along a common radial path relative to a center axis of the first portion. The first portion may include a cylindrical body portion.

The body of the second segment may include an actuation cable channel. The actuation cable channel may include a first opening at a diametric midpoint of the semi-spherical body portion of the second segment and a second opening at a diametric midpoint of the first portion of the second segment. The first portion may include a cylindrical body portion. The actuation cable channel may include an upper taper joined at the first opening that conforms the first opening with a first cylindrical cavity of the body of the second segment. The first cylindrical cavity may join a second cylindrical cavity of the body of the second segment. A diameter of the first cylindrical cavity may be less than a diameter of the second cylindrical cavity.

The second segment link may be coupled to the functional element. The second segment link may be coupled to a connection link of the functional element. The connection link may include a material selected from the group consisting of: metal, plastic, a thermoplastic polymer, stainless steel, polyvinyl chloride and a liquid-crystal polymer.

The functional element may include an actuating piston positioned within an inner cavity of the connection link. The actuation piston may include a material selected from the group consisting of: metal, plastic, a thermoplastic polymer, stainless steel, polyvinyl chloride and a liquid-crystal polymer. The functional element may further include first and second actuation link members coupled to the actuating piston. The first and second actuation link members may include a material selected from the group consisting of: metal, plastic, a thermoplastic polymer, stainless steel, polyvinyl chloride and a liquid-crystal polymer. The functional element may further include first and second claw members respectively coupled to the first and second actuation link members. The first and second claw members may include a material selected from the group consisting of: metal, plastic, a thermoplastic polymer, stainless steel, polyvinyl chloride and a liquid-crystal polymer. Linear movement of the actuating piston within the inner cavity of the connection link may cause the first and second claw members to open and close. An actuating cable may be coupled to the actuating piston. The actuating cable may include one or more selected from the group consisting of: a metal cable, a plastic cable, a sold wire cable, a braided cable and a stainless steel wire braided cable.

The at least two segment links may include a material selected from the group consisting of: metal, plastic, a thermoplastic polymer, stainless steel, polyvinyl chloride, a liquid-crystal polymer and polytetrafluoroethylene. The first segment link may include a material selected from the group consisting of: metal, plastic, a thermoplastic polymer, stainless steel, polyvinyl chloride, a liquid-crystal polymer and polytetrafluoroethylene. The second segment link may include a material different from the first segment link.

In some embodiments, a first segment link of the at least two segment links may be coupled to a first shaft portion of the tool shaft, and a second segment link of the at least two segment links is coupled to one of a second shaft portion of the tool shaft and the functional element. The first shaft portion of the tool shaft includes a cable transitioning segment.

The cable transitioning segment may include at least one articulation cable channel. The at least one articulation cable channel may comprise first through fourth articulation cable channels that are spaced 90° apart around the circumference of the cable transitioning segment. At least two articulation cable channels of the cable transitioning segment may be aligned with at least two articulation cable channels of the first segment link.

The cable transitioning segment may include an actuation cable channel. The actuation cable channel may be positioned at a diametric midpoint of the cable transitioning segment. The cable transitioning segment may include a material selected from the group consisting of: metal, plastic, a thermoplastic polymer, stainless steel, polyvinyl chloride, a liquid-crystal polymer, and polytetrafluoroethylene.

The first shaft portion of the tool shaft may include a flexible tool shaft portion. The flexible tool shaft portion may include a lumen guiding member having at least one cable channel. The at least one cable channel may include an actuating cable channel and at least one articulation cable channel. The actuating cable channel may be positioned at a diametric midpoint of the flexible tool shaft portion, and the at least one articulation cable channel may be positioned along a circumference of the flexible tool shaft portion. The lumen guiding member includes a five lumen stiffening rod. The lumen guiding member may include a material selected from the group consisting of: metal, plastic, a thermoplastic polymer, stainless steel, polyvinyl chloride, a liquid-crystal polymer, and polytetrafluoroethylene.

At least one cavity slot may be formed in the bottom surface of the first portion of the second segment. The at least one cavity slot may include a first cavity slot and a second cavity slot. The first cavity slot may extend from a first articulation cable channel of the at least one articulation cable channel to a second articulation cable channel of the at least one articulation cable channel. A first articulation cable may be positioned within the first articulation cable channel, the first cavity slot and the second articulation cable channel. The first articulation cable may be secured to a surface of the first cavity slot. The first articulation cable may be welded to the surface of the first cavity slot. The first articulation cable may be glued to the surface of the first cavity slot. The first articulation cable may be press fit within the first cavity slot. The second cavity slot may extend from a third articulation cable channel of the at least one articulation cable channel to a fourth articulation cable channel of the at least one articulation cable channel. A second articulation cable may be positioned within the third articulation cable channel, the second cavity slot and the fourth articulation cable channel.

The at least one cavity slot may extend along an entire circumference of the bottom surface of the cylindrical body portion of the second segment. The second opening of the at least one articulation cable channel may be partially defined by the at least one cavity slot. At least one articulation cable may be positioned within the at least one articulation cable channel, and wherein the at least one articulation cable may be secured to a surface of the at least one cavity slot.

In some embodiments, the articulation region of the tool shaft may include a plurality of segment links. Each segment link of the plurality of segment links may be sequentially coupled to another segment link of the plurality of segment links. The plurality of segment links may articulate with respect to one another. A bottom surface of a first portion of a first segment link of the plurality of segment links may abut an upper surface of a first portion of a second segment link of the plurality of segment links to restrict an angle of articulation with respect to a center axis of each of the first and second segment links. The angle of articulation may be restricted to 12° to 15°.

The first portion of the first segment link may include a cylindrical body portion and the first portion of the second segment link may include a cylindrical body portion. Each segment link of the plurality of segment links may be constructed and arranged to provide 12° to 15° of articulation between the functional element and a working surface of the articulating probe. Each segment link of the plurality of segment links may be constructed and arranged to provide 12° to 15° of articulation between the functional element and a longitudinal axis of a cable transitioning segment of the tool shaft. Each segment link of the plurality of segment links may be constructed and arranged to provide 12° to 15° of articulation between the functional element and an axis of extension of the tool shaft.

In some embodiments, the articulation region may be constructed and arranged to support a force of approximately 1 $lb_F$ without deflecting more than approximately ½ inch.

In some embodiments, the articulation region may be constructed and arranged to support a force of approximately 1 $lb_F$ without deflecting more than approximately ½ inch when in a fully articulated state.

In another aspect, a surgical tool comprises: a functional element positioned at a distal end of a tool shaft; and a tool handle positioned at a proximal end of the tool shaft, wherein the tool shaft includes an articulation region.

In some embodiments, the articulation region may be positioned at the distal end of the tool shaft between the functional element and a first portion of the tool shaft.

In some embodiments, the articulation region may be positioned at a central region of the tool shaft. The articulation region may be positioned between a first portion of the tool shaft and a second portion of the tool shaft. The tool handle may be coupled to a proximal end of the first portion of the tool shaft.

The articulation region may include a plurality of segment links. Each segment link of the plurality of segment links may be constructed and arranged to provide 12° to 15° of articulation between the functional element and an axis of the tool shaft. A first segment link of the plurality of segment links may be coupled to a first portion of the tool shaft and a second segment of the plurality of segment links is coupled to the functional element.

The first segment link may include a body having a first portion and a second portion, wherein the second portion includes a semi-spherical body portion. The first portion may include a cylindrical body portion.

The second segment link may include a body having a first portion and a second portion, wherein the second portion includes a semi-spherical body portion. The first portion may include a cylindrical body portion.

The semi-spherical body portion of the first segment link may mate with a semi-spherical cavity portion of the first portion of the tool shaft and wherein the semi-spherical body portion of the second segment link may mate with a semi-spherical cavity portion of the first segment link. The functional element may include a connection link having a semi-spherical body portion that mates with a semi-spherical cavity portion of the second segment link.

Each of the plurality of segment links may include a body having a first portion and a second portion, wherein the second portion may include a semi-spherical body portion, and wherein each of the plurality of segment links may include at least one articulation cable channel and an actuating cable channel. The first portion may include a cylindrical body portion.

At least one articulation cable may be positioned within the at least one articulation cable channel. The at least one articulation cable may be secured to a distal segment link of the plurality of segment links. A tension applied to the at least one articulation cable may cause the functional element to articulate with respect to the tool shaft.

An actuating cable may be positioned within the actuating cable channel. A tension applied to the actuating cable may cause the functional element to change state.

In some embodiments, the tool shaft includes a five-lumen extrusion positioned within a wire coil. A tool shaft cover may surround the wire coil. The tool shaft cover may include a Pebax®-type shaft cover.

In another aspect, a surgical tool comprises: a functional element positioned at a distal end of a tool shaft; and a tool handle positioned at a proximal end of the tool shaft, wherein the tool shaft includes an articulation region.

In some embodiments, the articulation region may include a plurality of segment links. A first segment link of the plurality of segment links may include a body having first and second concave cavities formed at opposite end surfaces of the body. The first concave cavity may be a semi-spherical cavity. The first concave cavity may be a semi-ellipsoidal cavity. The second concave cavity may be a semi-spherical cavity. The second concave cavity may be a semi-ellipsoidal cavity.

A second segment link of the plurality of segment links may include a body having first and second convex body portions formed at opposite end surfaces of a center body portion. The first convex body portion may be a semi-spherical body portion. The first convex body portion may be a semi-ellipsoidal body portion. The second convex body portion may be a semi-spherical body portion. The second convex body portion may be a semi-ellipsoidal body portion. The center body portion may be cylindrical.

One of the first and second convex body portions of the second segment link may mate with one of the first and second concave cavities of the first segment link. The other of the first and second convex body portions of the second segment link may mate with a concave cavity of the tool shaft. The other of the first and second concave cavities of the first segment link may mate with a convex body portion of a third segment link of the plurality of segment links. The third segment link may be coupled to the functional element.

In some embodiments, a first segment link of the plurality of segment links may include a first body having a first protrusion extending from a surface of the first body. The first body may be a cylindrical body. The first body may have an elliptical cross-section. The first protrusion may be a cylindrical protrusion. The first protrusion may have an elliptical cross-section.

A second segment link of the plurality of segment links may include a second body having a second protrusion extending from a first surface of the second body. The second body may be a cylindrical body. The second body may have an elliptical cross-section. The second protrusion may be a cylindrical protrusion. The second protrusion may have an elliptical cross-section.

The second segment link may include a concave cavity formed in a second surface of the second body. The concave cavity may be a semi-spherical cavity. The concave cavity may be a semi-ellipsoidal cavity. The first protrusion of the first segment link may mate with the concave cavity of the second segment link. The first segment link may be coupled to the functional element. The second protrusion of the second segment link may mate with a concave cavity of the tool shaft.

In some embodiments, a first segment link of the plurality of segment links may include a body having a first body portion and a second body portion. The first body portion may include a cylindrical body portion. The first body portion may have an elliptical cross-section. The second body portion may include a convex body portion. The convex body portion may be a semi-spherical body portion. The convex body portion may be a semi-ellipsoidal body portion.

A second segment link of the plurality of segment links may include a body having center body portion, a convex body portion coupled to a first surface of the center body portion, and a plurality of posts extending outwardly from a second surface of the center body portion. The convex body portion may be a semi-spherical body portion. The convex body portion may be a semi-ellipsoidal body portion. The center body portion may be cylindrical. The center body portion may have an elliptical cross-section. The plurality of posts may be cylindrical. The plurality of posts may have elliptical cross-sections. The plurality of posts may include one of rounded or beveled upper edges.

The plurality of posts may be arranged along a common radial path relative to a center axis the second surface of the center body portion. The plurality of posts may include a center post and two or more outer posts, the center post being positioned at a diametric midpoint of the second surface. The two or more outer posts may be arranged along a common radial path relative to the center post. The outer posts may be equally spaced apart. The two or more outer posts may each have a first height greater than a second height of the center post.

The second body portion of the first segment link may mate with the plurality of posts extending outwardly from the second surface of the center body portion. The convex body portion of the second segment link may mate with a plurality of posts of a third segment link of the plurality of segment links. The third segment link may be coupled to the tool shaft.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same elements throughout the different views. The drawings are not necessarily to scale, emphasis instead being placed upon illustrating the principles of the preferred embodiments.

FIG. 4C is a cross-sectional perspective view of the segment links illustrated at FIG. 4, in accordance with embodiments of the present inventive concepts;

FIGS. 5A and 5B are perspective views illustrating articulation ranges of the articulating surgical tool illustrated at FIG. 2, in accordance with embodiments of the present inventive concepts;

FIG. 6A is a side perspective view illustrating an alternative segment link configuration of an articulating surgical tool, in accordance with embodiments of the present inventive concepts;

FIG. 6B is a side perspective view illustrating an alternative segment link configuration of an articulating surgical tool, in accordance with embodiments of the present inventive concepts;

FIG. 6C is a sectional view of the third segment links illustrated in FIG. 6B, in accordance with embodiments of the present inventive concepts;

DETAILED DESCRIPTION OF EMBODIMENTS

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

Figure 1A:
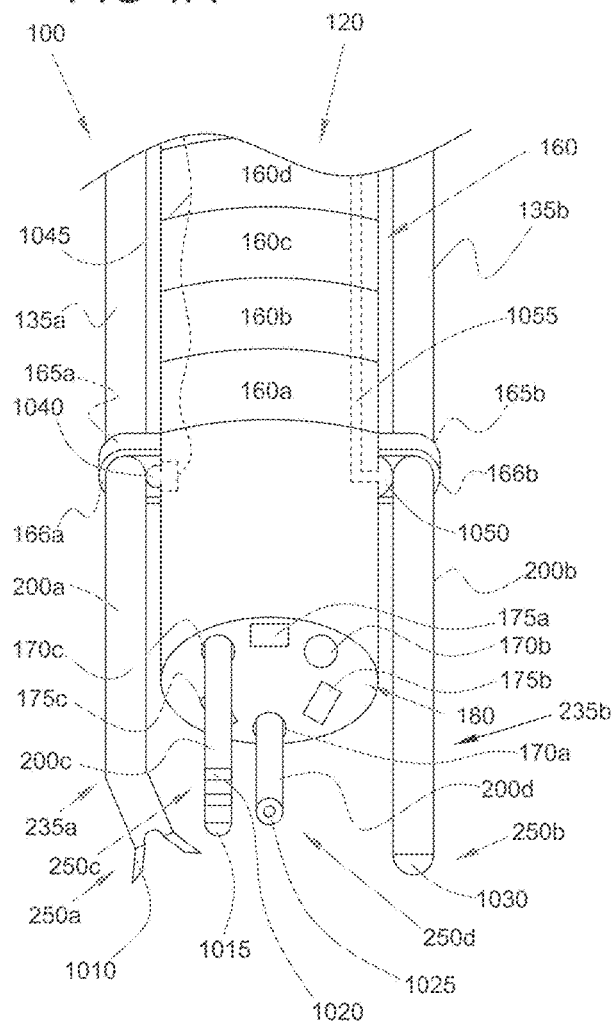
FIG. 1A is a perspective view of an articulating probe of a system for performing a medical procedure, in accordance with embodiments of the present inventive concepts.
Figure 1B:
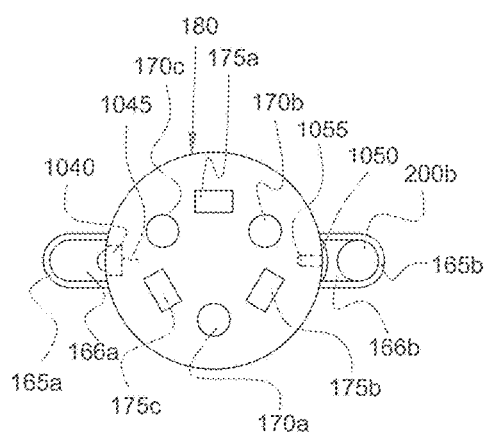
FIGS. 1B and 1C are end views of a working surface of the articulating probe illustrated at FIG. 1A, in accordance with embodiments of the present inventive concepts.
Figure 1C:
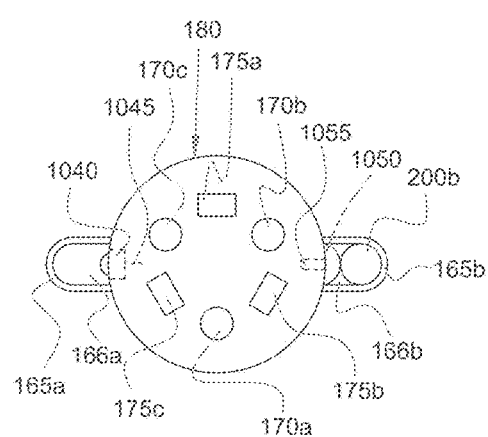
Figure 1D:
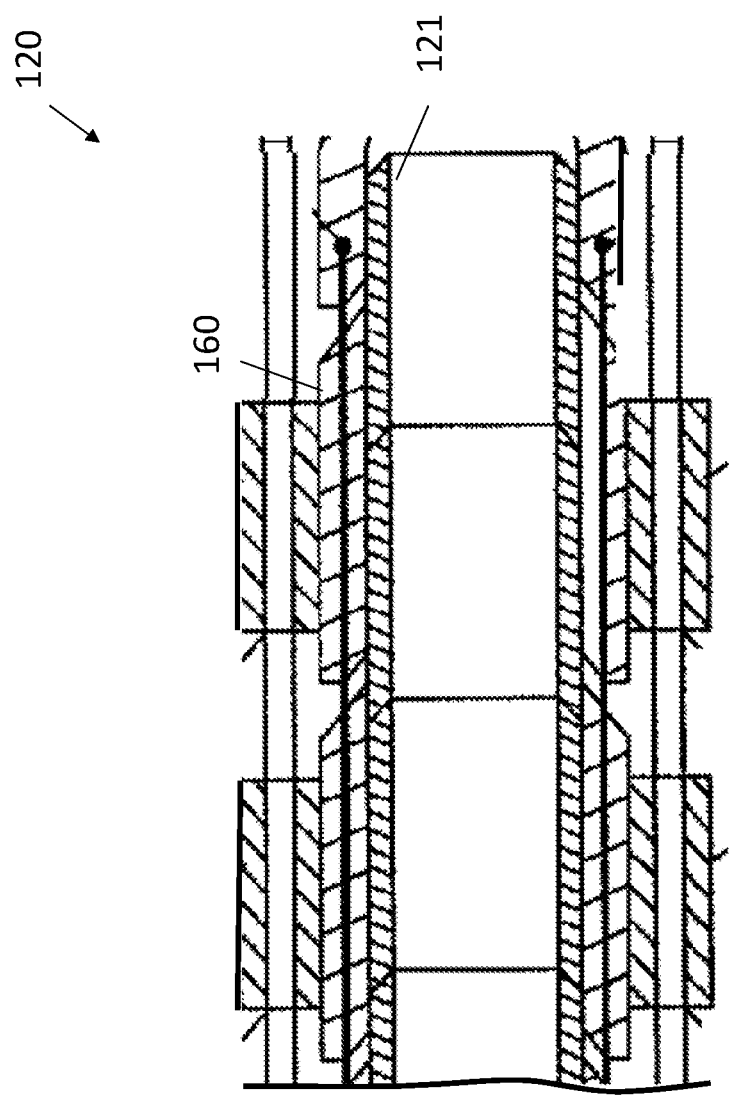
FIG. 1D is a cross-sectional side view of a distal portion of the articulating probe illustrated at FIGS. 1A-1C, in accordance with embodiments of the present inventive concepts.

FIG. 1A is a perspective view of an articulating probe of a system for performing a medical procedure, and FIGS. 1B and 1C are end views of a working surface of the articulating probe illustrated at FIG. 1A. A system 100 for performing a medical procedure, such as a transoral robotic surgery procedure, may include an articulating probe 120 for guiding one or more surgical tools 200, 200a-d and/or tool sheaths 200, 200a within a patient body. The system 100 may include one or more features of the surgical positioning and support system described in U.S. Provisional Patent Application Ser. No. 61/368,257, filed Jul. 28, 2010 corresponding to PCT application serial number PCT/US2011/044811, filed Jul. 21, 2011, the contents of which are herein incorporated by reference in their entirety.

An operator, such as a medical professional, may control the articulating probe 120 via a human interface device (HID) to manipulate or otherwise control the functions and movement of the articulating probe 120. The HID may include one selected from the group consisting of: a haptic controller, a joystick, a track ball, a mouse and an electromechanical device.

The articulating probe 120 may include an inner sleeve 121 and an outer sleeve 160, which can advance or retract with respect to one another during manipulation of the articulating probe 120. For example, the inner and outer sleeves of the articulating probe 120, which may include a plurality of inner links and a plurality of outer links 160, 160a-d, can be configured in one of a limp mode and a rigid mode so as to facilitate the manipulation of the articulating probe 120. For example, the inner and outer sleeves may be configured in one of the limp mode and the rigid mode via one or more steering cables of the articulation probe 120.

Exemplary probes are further described in U.S. Patent Application Publication No. 2009/0171151, published on Jul. 2, 2009, by Choset, et al., and U.S. Patent Application Publication No. 2008/0039690, published Feb. 14, 2008, by Zubiate, et al., the contents of each being herein incorporated by reference in their entirety.

The articulating probe 120 may include at least one working channel 170, 170a-c having an opening at a working surface 180 of the articulating probe 120. The working channel 170, 170a-c may extend throughout the articulating probe 120, for example, from a proximal end to a distal end of the articulating probe 120. The working surface 180 may be positioned at a distal end of the articulating probe 120. For example, the working surface 180 may be positioned at a distal end of an outer distal link 160a of the articulating probe 120.

The articulating probe 120 may include at least one side port or guide hole 166, 166a-b. For example, in the embodiments shown at FIG. 1, the articulating probe 120 includes first and second side ports 166a, 166b formed in flanges 165a, 165b of an outer link 160a. The articulating probe 120 may further include at least one feed tube 135, 135a-b coupled to the side port or guide hole 166, 166a-b of the articulating probe 120.

Although first and second side ports 166a, 166b are shown at FIG. 1A, a plurality of first and second side ports 166a, 166b may be formed in a plurality of flanges 165a, 165b of the articulating probe 120. For example, multiple first and/or second side ports 166a, 166b may be positioned along the outer sleeve 160 of the articulating probe 120 so as to provide a guide for one or more feed tubes 135, 135a-b that articulate in common with the articulating probe 120.

The articulating probe may include one or more light sources 175, 175a-c provided at the working surface 180 of the articulating probe 120. The light sources 175, 175a-c may include electron stimulated light sources such as electron stimulated luminescence light sources, incandescent light sources such as incandescent light bulbs, electroluminescent light sources such as light-emitting diodes, and gas discharge light sources such as fluorescent lamps.

The light sources 175, 175a-c may further include optical fibers, which can be configured to transmit light to and from the working surface 180 of the articulating probe 120.

The system 100 may further include one or more surgical tools 200, 200a-d having an articulation region 235, 235a-b. The system 100 may be configured to allow an operator to independently control the articulating probe 120 and the surgical tools 200, 200a-d. For example, the articulating probe 120 may be controlled via a HID and the surgical tools 200, 200a-d may be controlled via a tool handle (see for example, tool handle 205 shown at FIG. 2).

The system 100 may be configured with any number of surgical tools 200, 200a-d, which can be slidably positioned within a working channel 170, 170a-c of the articulating probe 120 and/or a side port 166, 166a-b or guide hole 166, 166a-b of the articulating probe 120.

The articulating probe 120 may be configured to guide one or more surgical tools 200, 200a-d, for example, during a medical procedure. For example, prior, during or after a medical procedure, a portion of the surgical tool shaft may be positioned within at least one of the working channels 170, 170a-c of the articulating probe 120. The articulating probe 120 may be further configured to allow an operator to slidably position the surgical tool shaft within at least one of the working channels 170, 170a-c so that a functional element 250, 250a-b of the surgical tool 200, 200a-d can be extended outwardly from a working channel opening.

In a further example, prior, during or after a medical procedure, a portion of the surgical tool shaft may be positioned within at least one side port or guide hole 166, 166a-b of the articulating probe 120. The articulating probe 120 may be further configured to allow an operator to slidably position the surgical tool shaft within at least one of the side ports or guide holes 166, 166a-b so that a functional element 250, 250a-b of the surgical tool 200, 200a-d can be extended outwardly from the working surface 180 of the articulating probe 120. A portion of the surgical tool shaft may pass through at least one side port or guide hole 166, 166a-b of the articulating probe 120, such that the side port or guide hole 166, 166a-b guides the surgical tool shaft along an outer surface of the outer sleeve 160 of the articulating probe 120.

The articulating probe 120 may include side port or guide hole locks 1040, 1050, which can be configured in one of a locked or unlocked mode. The lock 1040, 1050 may be constructed to secure a position of a surgical tool 200, 200a-b positioned within the side ports or guide holes 166, 166a-b of the articulating probe 120, thus preventing the surgical tool 200, 200a-b from sliding within the side ports or guide holes 166, 166a-b.

In some embodiments, the articulating probe 120 may include a pneumatic or hydraulic lock 1050, such as a solenoid or air/fluid pouch. For example, the pneumatic or hydraulic lock 1050 may be positioned within the side ports or guide holes 166, 166a-b of the articulating probe 120. The articulating probe 120 may further comprise a channel or tube 1055 for supplying pressurized gas or liquid to the pneumatic or hydraulic lock 1050.

In some embodiments, the articulating probe 120 may include an electrically activated lock 1040, such as a solenoid, piezoelectric actuator or nitinol actuated lock. For example, the electrically activated lock 1040 may be positioned within the side ports or guide holes 166, 166a-b of the articulating probe 120. The articulating probe 120 may further comprise a conductor 1045 such as a wire or cable for supplying an actuating signal to the electrically activated lock 1040.

Referring to FIG. 1B, the electrically activated lock 1040 is shown positioned within the first side port or guide hole 166a of the articulating probe 120, and the pneumatic or hydraulic lock 1050 is shown positioned within the second side port or guide hole 166b of the articulating probe 120. In this illustration, the electrically activated lock 1040 and the pneumatic or hydraulic lock 1050 are shown in the unlocked mode so as to allow an operator or user of the system 100 to slidably position a surgical tool shaft within the side port or guide holes 166, 166a-b of the articulating probe 120.

Referring to FIG. 1C, the pneumatic or hydraulic lock 1050 is shown in the locked mode. In the locked mode, the pneumatic or hydraulic lock 1050 expands within the side port or guide hole 166, 166b so as to secure the shaft of the surgical tool 200, 200b within the side port or guide hole 166, 166b. Although not shown, the electrically activated lock 1040 may be configured to expand within the side port or guide hole 166, 166a so as to secure the shaft of the surgical tool 200, 200a within the side port or guide hole 166, 166a.

The functional element 250, 250a-b may be constructed and arranged to articulate with respect to the working surface 180 of the articulating probe 120. For example, in the embodiments shown at FIG. 1A, the functional elements 250a, 250b are shown articulated with respect to the working surface 180 of the articulating probe 120. The functional elements 250, 250a, 250b may also be constructed and arranged to articulate with respect to an axis of extension of the tool shaft.

The functional element 250, 250a-b may be constructed and arranged to articulate between 0° and 90° with respect to the working surface 180 of the articulating probe 120 and/or an axis of extension of the tool shaft. The functional element 250, 250a-b may be constructed and arranged to articulate between 0° and 135° with respect to the working surface 180 of the articulating probe 120 and/or an axis of extension of the tool shaft. The functional element 250, 250a-b may be constructed and arranged to articulate between 0° and 180° with respect to the working surface 180 of the articulating probe 120 and/or an axis of extension of the tool shaft. The functional element 250, 250a-b may be constructed and arranged to articulate at an angle greater than 180° with respect to the working surface 180 of the articulating probe 120 and/or an axis of extension of the tool shaft.

The functional element 250 may include one or more selected from the group consisting of: a grasper, a claw, a cutter, a knife, an ablator, a cauterizer, a drug delivery apparatus, a radiation source, an EKG electrode, a pressure sensor, a blood sensor, a camera, a magnet, a heating element and a cryogenic element. For example, the functional element 250a of a first surgical tool 200a may include a cutter having first and second blades 1010. The functional element 250b of a second surgical tool 200b may include a heating element, cryogenic element, a pressure sensor, a blood sensor and/or a radiation source 1030. The functional element 250c of a third surgical tool 200c may include one or more EKG electrodes or heart defibrillator electrodes 1015, 1020. The functional element 250d or a fourth surgical tool 200d may include a camera 1025.

Figure 2:
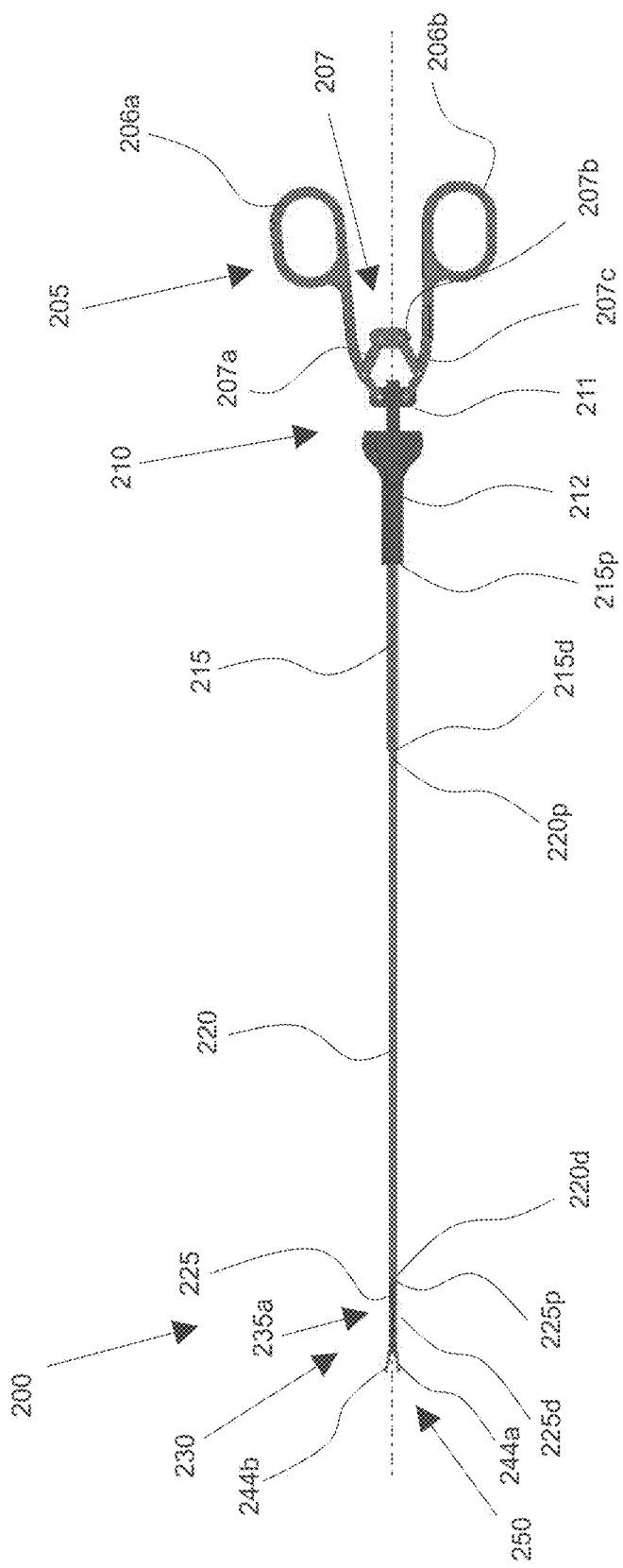
FIG. 2 is a perspective view of an articulating surgical tool, in accordance with embodiments of the present inventive concepts.

FIG. 2 is a perspective view of an articulating surgical tool. A surgical tool 200 may include a tool handle 205, a surgical tool shaft 215, 220 having an articulation region 235 and a functional element 250.

The surgical tool 200 may be constructed and arranged to be controlled via a surgical tool handle 205. The surgical tool handle 205 may include one selected from the group consisting of: scissor handles, a palm-held grip, a thumb/index/middle finger grip and a pistol grip. For example, in the embodiment shown in FIG. 2, the surgical tool handle 205 includes first and second actuating handle elements 206a, 206b that are coupled at a ball mechanism 211 and a handle link mechanism 207. The handle link mechanism 207 may include first and second links 207a, 207c that are coupled at a link body 207b.

In this exemplary embodiment, the surgical tool includes a ball mechanism 211 that is constructed and arranged to be coupled to a socket mechanism 212 for manipulating or otherwise controlling the functions and movement of the surgical tool 200. Although not shown, one or more articulation cables 410 may be secured to the ball mechanism 211, and one or more actuating cables 420 may be secured to the link body 207b of the handle link mechanism 207. In this manner, a movement of the ball mechanism 211 with respect to the socket mechanism 212 can provide tension or slack on one or more of the articulation cables 410 secured to the ball mechanism 211, thereby adjusting an articulation state of articulation region 235. In addition, a scissoring movement of the first and second actuating handle elements 206a, 206b can cause the link body 207b of the link mechanism 207 to extend outwardly (e.g., along the longitudinal axis) from the ball mechanism 211, thereby applying a tension on the one or more actuating cables 410.

The surgical tool shaft 215, 220 may include a first tool shaft 215 and second tool shaft 220. A proximal end 215p of the first tool shaft 215 may be coupled to the tool handle 205, for example, via the ball and socket mechanisms 211, 212, and a distal end 215d of the first tool shaft 215 may be coupled to a proximal end 220p of the second tool shaft 220. A distal end 220d of the second tool shaft 220 may be directly coupled to the articulation region 235 or indirectly coupled to the articulation region 235. For example, in the embodiments shown in FIGS. 2 and 3A, the distal end 220d of the second tool shaft 220 is coupled to the articulation region 235 through an optional cable transitioning segment 225.

Although the articulation region 235 is shown at a distal end 230 of the surgical tool 200, the articulation region 235 may be provided at any position between the functional element 250 and the proximal end 215p of the first tool shaft 215.

The articulation region 235 may be constructed and arranged to support a force of approximately 1 $lb_F$ without deflecting more than approximately ½ inch. In some embodiments, the articulation region 235 is constructed and arranged to support a force of approximately 1 $lb_F$ without deflecting more than approximately ½ inch when in a fully articulated state.

Figure 3A:
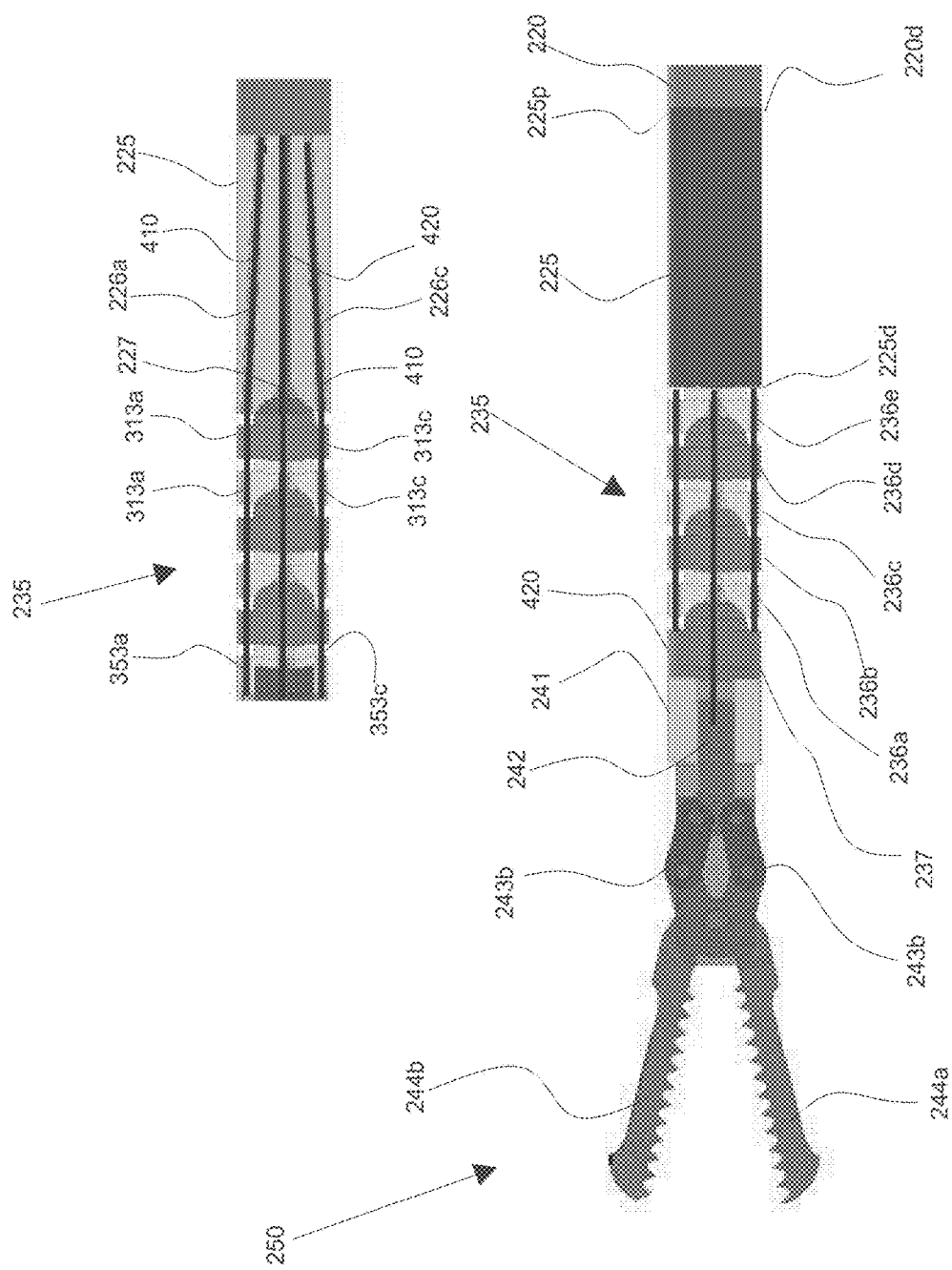
FIGS. 3A and 3B are perspective views of a distal end of the articulating surgical tool illustrated at FIG. 2, in accordance with embodiments of the present inventive concepts.
Figure 3B:
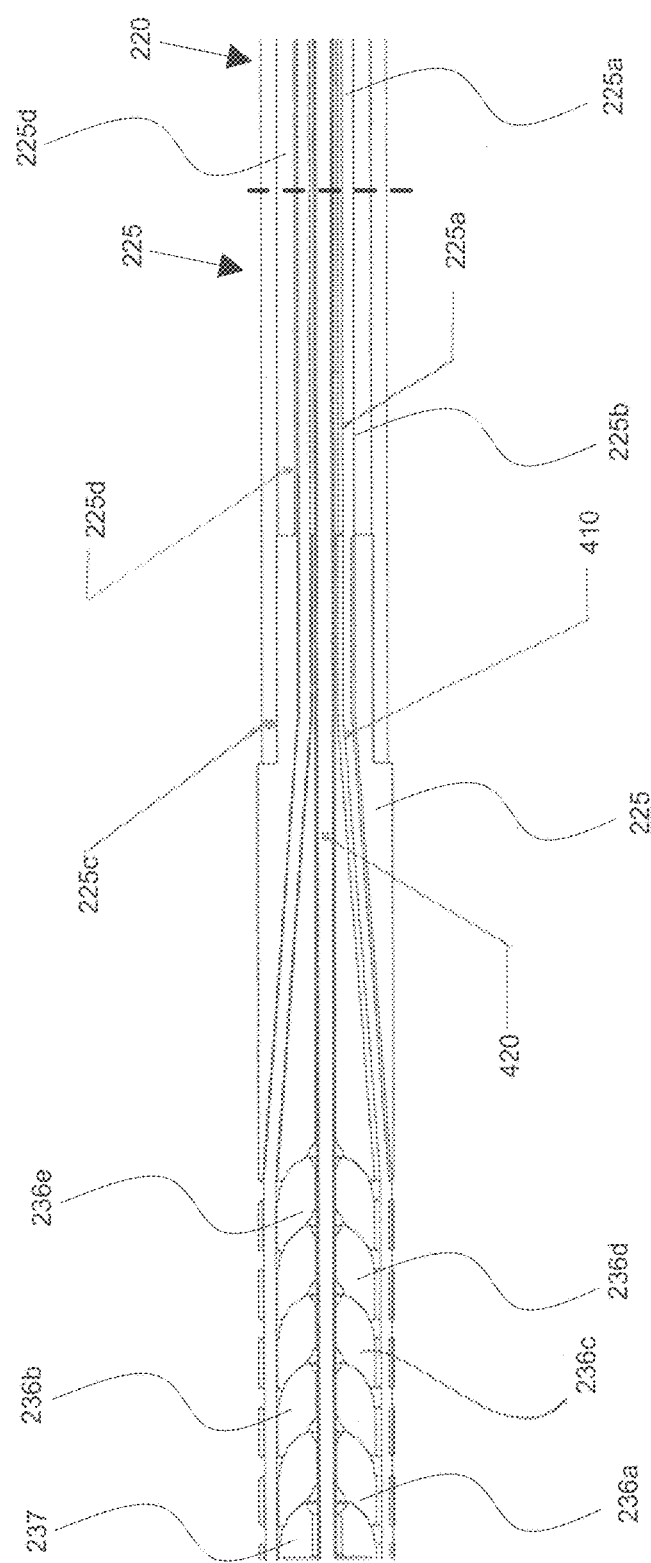

Referring to FIGS. 3A and 3B, the cable transitioning segment 225 may include at least one articulation cable channel 226. For example, the at least one articulation cable channel 226 may include first through fourth articulation cable channels 226 that are spaced 90° apart around the circumference or perimeter of the cable transitioning segment 225. At least two articulation cable channels 226a, 226c of the cable transitioning segment 225 may be aligned with at least two articulation cable channels 313a, 313c of a first segment link 236 of the articulation region 235 and/or at least two articulation cable channels 353a, 353c of a second segment link 237 of the articulation region 235. In this manner, one or more articulation cables 410 can be positioned within the cable channels 313a, 313c, 353a, 353c of the first and second segment links 236, 237.

In some embodiments, the cable transitioning segment 225 may include n number of articulation cable channels 226, where n is a real number greater than 0. For cases where n is greater than 1, the n number of articulation cable channels 226 may be evenly spaced apart around the circumference or perimeter of the cable transitioning segment 225 or it may not.

The cable transitioning segment 225 may include an actuation cable channel 227. The actuation cable channel 227 may be positioned at a diametric midpoint of the cable transitioning segment 225, and may be aligned with one or more actuation cable channels 314, 354 of one or more segment links 236, 237 of the articulation region 235. In this manner, one or more actuation cables 420 can be positioned within the cable channels 314, 354 of the first and second segment links 236, 237.

The cable transitioning segment 225 may include a material selected from the group consisting of: metal, plastic, a thermoplastic polymer, stainless steel, polyvinyl chloride, a liquid-crystal polymer, polytetrafluoroethylene, and a combination of these materials or other suitable material.

Referring to FIG. 3B, the cable transitioning segment 225 and/or the surgical tool shaft 220 may comprise a lumen extrusion 225a positioned within a wire coil 225b, such as a flat wire coil or spring. The wire coil 225b may increase a stiffness of the cable transitioning segment 225 and/or the surgical tool shaft 220 so as to prevent twisting and/or kinking of the surgical tool 200. The wire coil 225b may further increase a radial stiffness of the cable transitioning segment 225 and/or the surgical tool shaft 220 so as to prevent a radial collapse of tool shaft and/or to prevent pinching the cables 410, 420. A tool shaft cover 225c such as a Pebax®-type shaft cover may be provided to cover the wire coil 225b.

Referring back to FIG. 2, the first tool shaft 215 may include a rigid tool shaft and the second tool shaft 220 may include a flexible tool shaft; however, the tool shafts 215, 220 of the surgical tool 200 may both include rigid or flexible tool shafts. That is, the first and second tool shafts 215, 220 of the surgical tool 200 may include any combination of rigid and flexible tool shafts.

The flexible tool shafts 215, 220 may include a lumen guiding member having at least one cable channel. In some embodiments, the at least one cable channel includes an actuating cable channel and at least one articulation cable channel. The actuating cable channel may be positioned at a diametric midpoint of the flexible tool shaft, and the at least one articulation cable channel may be positioned along a circumference or perimeter of the flexible tool shaft portion. For example, the lumen guiding member may include a five lumen stiffening rod having an actuating cable channel and first through fourth articulation cable channels.

The lumen guiding member may include a material selected from the group consisting of: metal, plastic, a thermoplastic polymer, stainless steel, polyvinyl chloride, a liquid-crystal polymer, polytetrafluoroethylene, and a combination of these materials or other suitable material.

The functional element 250 of the surgical tool 200 may be provided at the distal end 230 of the surgical tool 200. The functional element 250 may include one or more selected from the group consisting of: a grasper, a claw, a cutter, a knife, an ablator, a cauterizer, a drug delivery apparatus, a radiation source, an EKG electrode, a pressure sensor, a blood sensor, a camera, a magnet, a heating element and a cryogenic element. For example, in the embodiments shown at FIGS. 2 and 3, the functional element 250 includes a grasper having first and second grasping members 244a, 244b. The grasper may be constructed and arranged to apply a grasping force of approximately 1 $lb_F$. The grasper may be further constructed and arranged to apply a grasping force of approximately 1 $lb_F$ when the articulation region is positioned in a fully articulated state. The grasper may be further constructed and arranged to apply a substantially similar grasping force throughout all articulation states of the articulation region 235 of the surgical tool 200 so that the operation of the grasper, or other type of functional element 250, is substantially maintained throughout the range of articulation of the surgical tool 200.

The surgical tool 200 may include a locking device that is constructed and arranged to lock an articulated position of the functional element 250. The surgical tool may further include a locking device that is constructed and arranged to lock an operational mode of the functional element 250. For example, the locking device can be constructed and arranged to lock the articulation state of the surgical tool 200, 200a-b and/or grasping state of the functional element 250 (e.g., opened, closed, partially closed).

The surgical tool 200 may be constructed and arranged to provide a cavity path for entry of a second surgical tool, such as a laser fiber or other elongate tool. For example, the functional element of a first surgical tool may include a first tool sheath cavity and the tool shaft of the first surgical tool may include a second tool sheath cavity. In this manner, a second surgical tool may be slidably positioned within the cavity path of the first surgical tool.

For example, referring to FIG. 1A, the first surgical tool 200a may be configured as a surgical tool sheath. The surgical tool sheath may have a sheath opening 165a formed at a distal end of the surgical tool 200a. A second surgical tool may be slidably positioned within a cavity path of the first surgical 200a so that a functional element of the second surgical can extend outward from the sheath opening 165a.

FIGS. 3A and 3B are perspective views of a distal end of the articulating surgical tool illustrated at FIG. 2. The articulation region 235 of the tool shaft may include a single segment link 236 or 237 or at least two segment links 236, 237. For example, in the embodiments shown at FIGS. 2, 3A and 3B, the articulation region 235 includes first through sixth segment links 236a-e, 237. The segment links 236, 236a-e, 237 may each be unitary in form, or may each be constructed of multiple portions of material that are bonded or coupled together.

A first segment link 236, 236e of the at least two segment links may be coupled directly or indirectly to the tool shaft 215, 220. For example, the first segment link 236, 236e of the at least two segment links 236, 237 may be coupled to the second tool shaft 220 via the cable transitioning segment 225, which may distribute multiple cables (e.g., one or more actuating cables 420 and/or one or more articulation cables 410) from the tool shaft 215, 220 to the channels of the segment links 236, 237.

A second segment link 237 of the at least two segment links 236, 237 may be coupled to the functional element 250. However, as described above, the articulation region 235 may be provided at any position between the functional element 250 and the proximal end 215p of the first tool shaft 215. For example, the first segment link 236, 236e of the at least two segment links 236, 237 may be coupled directly or indirectly to the first tool shaft 215, and a second segment link 237 of the at least two segment links may be coupled directly or indirectly to the second tool shaft 220.

The second segment link 237 may be coupled to the functional element 250. For example, the second segment link 237 may be coupled to a connection link 241 of the functional element 250. The connection link 241 may include a material selected from the group consisting of: metal, plastic, a thermoplastic polymer, stainless steel, polyvinyl chloride and a liquid-crystal polymer.

The functional element 250 may include an actuating piston 242 positioned within an inner cavity of the connection link 241. The actuation piston 242 may include a material selected from the group consisting of: metal, plastic, a thermoplastic polymer, stainless steel, polyvinyl chloride and a liquid-crystal polymer.

The functional element 250 may further include first and second actuation link members 243a-b coupled to the actuating piston 242. The first and second actuation link members may include a material selected from the group consisting of: metal, plastic, a thermoplastic polymer, stainless steel, polyvinyl chloride and a liquid-crystal polymer.

The functional element 250 may further include first and second claw members or grasper members 244a-b, which can be respectively coupled to the first and second actuation link members 243a-b. The first and second claw members or grasper members 244a-b may include a material selected from the group consisting of: metal, plastic, a thermoplastic polymer, stainless steel, polyvinyl chloride and a liquid-crystal polymer, a combination of these materials or other suitable material.

In the embodiment shown in FIG. 3A, linear movement of the actuating piston 242 within the inner cavity of the connection link 241 can cause the first and second claw members or grasper members 244a-b to open and close. The opening and closing of the first and second claw members or grasper members 244a-b may be in response to a tension applied to an actuating cable 420 coupled to the actuating piston 242. The actuating cable 420 may include one or more selected from the group consisting of: a metal cable, a plastic cable, a sold wire cable, a braided cable and a stainless steel wire braided cable.

Although the articulation region 235 of the surgical tool 200 shown in FIGS. 3A and 3B illustrate a plurality of segment links 236, 237 having convex body portions 312, 352 (e.g., semi-ellipsoidal body portions, semi-spherical body portions) being oriented in a directing facing away from the functional element 250, the surgical tool 200 can be configured to include an articulation region 235 having a plurality of segment links 236, 237 having convex body portions 312, 352 (e.g., semi-ellipsoidal body portions, semi-spherical body portions) oriented in a direction facing the functional element 250 as shown in FIG. 6A.

In some embodiments, alternating convex body portions 312, 352 of the segment links 236, 237 may be constructed and arranged to have different coefficients of friction when mated with corresponding concave cavity portions of adjacent segment links 236. For example, alternating convex body portions 312, 352 of the segment links 236, 237 may include different materials and/or coatings to adjust and/or alter the coefficient of friction when mated with corresponding concave cavity portions of adjacent segment links 236.

Figure 4A:
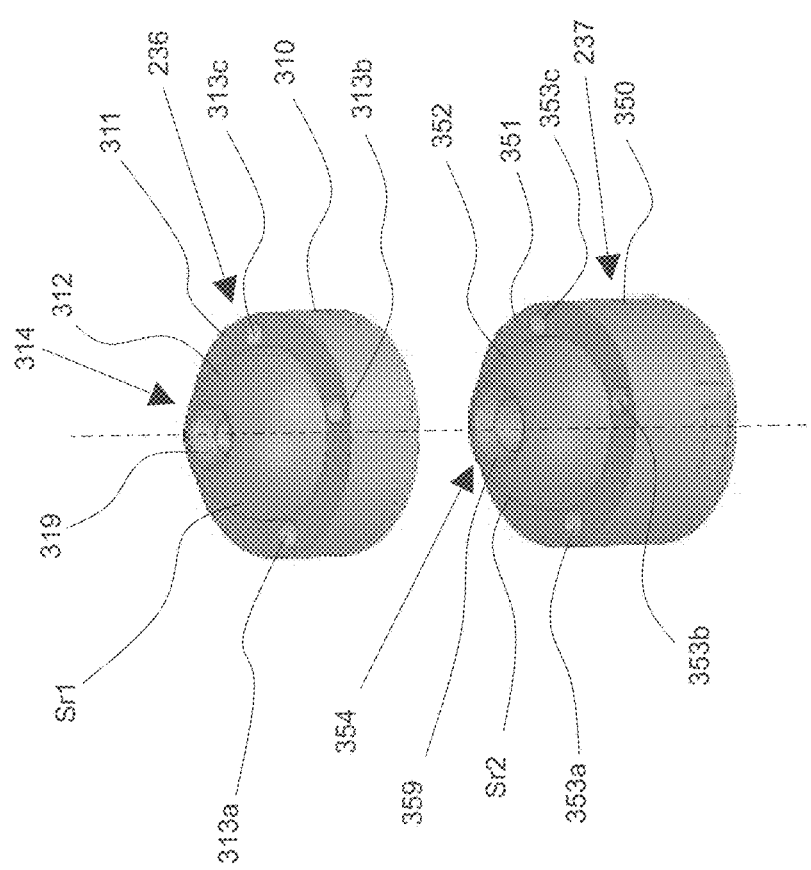
FIG. 4A is a perspective view of segment links of the articulating surgical tool illustrated at FIG. 3, in accordance with embodiments of the present inventive concepts.
Figure 4B:
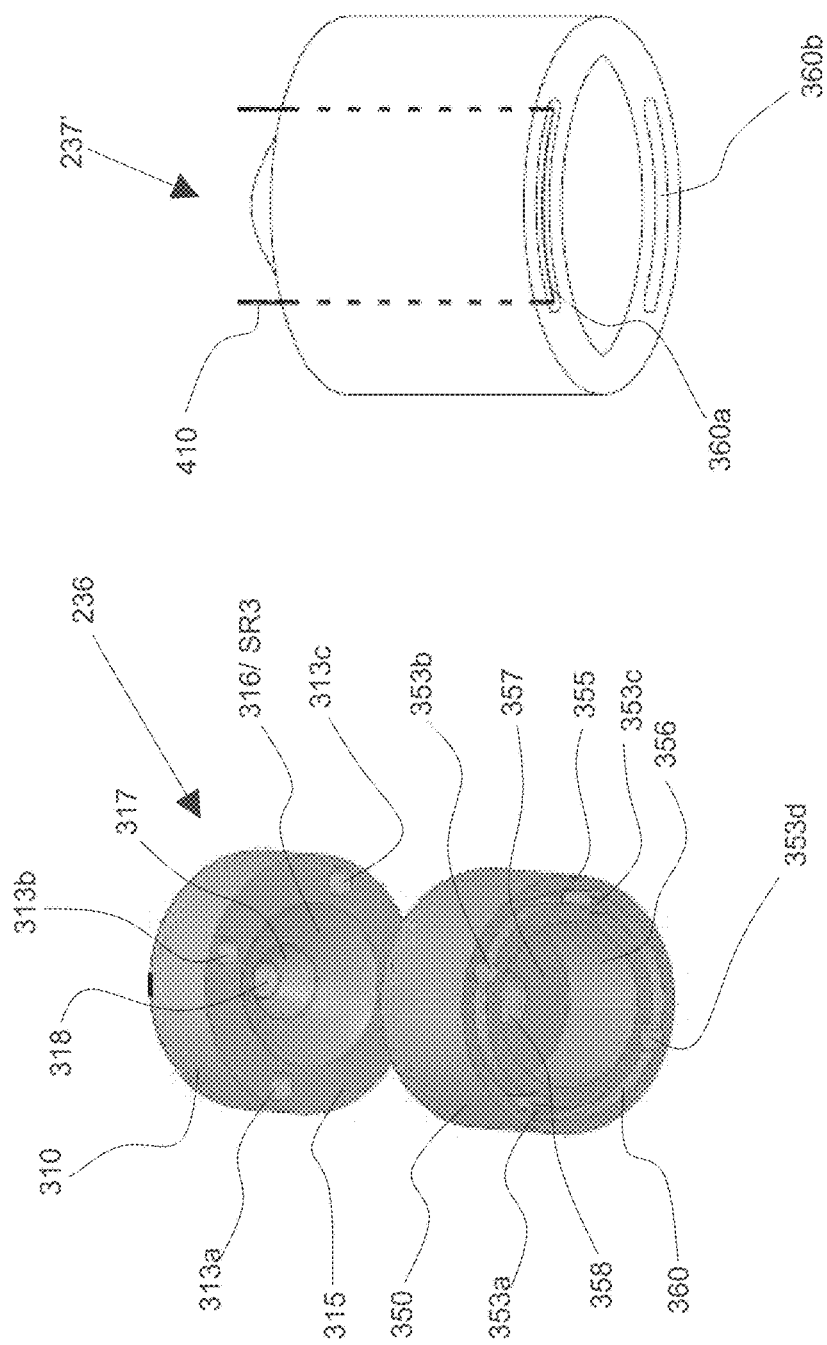
FIG. 4B is a perspective view of segment links of the articulating surgical tool illustrated at FIG. 3, in accordance with embodiments of the present inventive concepts.

FIG. 4A is a top perspective view of segment links of the articulating surgical tool illustrated at FIG. 3, FIG. 4B is a bottom perspective view of segment links of the articulating surgical tool illustrated at FIG. 3, and FIG. 4C is a cross-sectional perspective view of the segment links illustrated at FIG. 4B.

The first segment link 236, 236a-e may include a body having a first portion 310 and a second portion 312. The first portion 310 may include a cylindrical body portion or a body portion having an elliptical cross-section, and the second portion 312 may include a convex body portion, a semi-ellipsoidal body portion or a semi-spherical body portion.

In a case where the second portion 312 includes a semi-spherical body portion, the semi-spherical body portion may include an outer surface having a spherical radius SR1 ranging between $\frac{1}{20}$ of an inch and $\frac{1}{4}$ of an inch. For example, the spherical radius SR1 may be about $\frac{1}{20}$ of an inch.

Referring to FIG. 3, a semi-spherical body portion of the first segment link 236 may mate with a semi-spherical cavity portion of the cable transitioning segment 225 and/or the tool shaft 215, 220.

Referring back to FIGS. 4A-4C, the first segment link 236, 236a-e may include at least one articulation cable channel 313, 313a-d. The at least one articulation cable channel 313, 313a-d may include a first opening in an upper surface 311 of the first portion 310 and a second opening in a bottom surface 315 of the first portion 310. For example, in the embodiments shown at FIGS. 4A-4C, the at least one articulation cable channel 313, 313a-d may comprise first through fourth articulation cable channels 313a-d that are spaced 90° apart around the circumference or perimeter of the first portion 310. The at least one articulation cable channel 313, 313a-d may also comprise first through fourth articulation cable channels 313a-d that are positioned 90° apart from one another along a common radial path relative to a center axis of the first portion 310.

The first segment link 236, 236a-e may include an actuation cable channel 314. The actuation cable channel 314 may include a first opening at a diametric midpoint of the semi-spherical body portion of the first segment 236, 236a-e and a second opening at a diametric midpoint of the first portion 310 of the first segment 236, 236a-e.

The actuation cable channel 314 may include an upper taper 319 joined at the first opening that conforms the first opening with a cylindrical cavity 318 of the body of the first segment 236, 236a-e. The upper taper includes a draft angle $\alpha_1$, which can range between 0° and 45°. The cylindrical cavity 318 may join a lower taper 317 of the body of the first segment 236, 236a-e. The lower taper 317 may conform the cylindrical cavity 318 with a concave cavity or a semi-spherical cavity 316 of the body of the first segment 236, 236a-e. The lower taper includes a draft angle $\alpha_2$, which can range between 0° and 45°. The actuation cable channel 314 may include an upper taper 319 and/or a lower taper 317 to prevent pinching of an actuation cable 420 positioned within the actuation cable channel 314 during articulation states of the articulation region 235 of the surgical tool 200.

The semi-spherical cavity 316 of the body of the first segment 236, 236a-e may include an inner surface having a spherical radius SR3 ranging between ½0 of an inch and ¼ of an inch. For example, the spherical radius SR3 may be about ½0 of an inch. The spherical radius SR3 may be substantially similar to or greater than a spherical radius SR1, SR2 of the first and second segment links 236, 237 so that a semi-spherical body portion of one of the first and second segment links 236, 237 can mate with a semi-spherical cavity portion of another first segment link.

The second segment link 237 may include a body having a first portion 350 and a second portion 352. The first portion 350 may include a cylindrical body portion or a body portion having an elliptical cross-section, and the second portion 352 may include a convex body portion, a semi-ellipsoidal body portion or a semi-spherical body portion.

In the case where the second portion includes a semi-spherical body portion, the semi-spherical body portion may include an outer surface having a spherical radius SR2 ranging between ½0 of an inch and ¼ of an inch. For example, the spherical radius SR2 may be about ½0 of an inch.

Referring to FIG. 3A, the semi-spherical body portion of the second segment link 237 may mate with a semi-spherical cavity portion 316 of the first segment link 236.

Referring back to FIGS. 4A-4C, the second segment link 237 may include at least one articulation cable channel 353, 353a-d. The at least one articulation cable channel 353, 353a-d may include a first opening in an upper surface 351 of the first portion 350 and a second opening in a bottom surface 355 of the first portion 350. For example, in the embodiments shown at FIGS. 4A-4C, the at least one articulation cable channel 353, 353a-d may comprise first through fourth articulation cable channels 353a-d that are spaced 90° apart around the circumference or perimeter of the first portion 350. The at least one articulation cable channel 353, 353a-d may also comprise first through fourth articulation cable channels 353a-d that positioned 90° apart from one another along a common radial path relative to a center axis of the first portion 350.

Referring to FIG. 3A, at least two articulation cable channels 313, 313a-d of the first segment link 236, 236a-e may be aligned with at least two articulation cable channels 353, 353a-d of the second segment link 237 so as to provide a cable channel for the insertion of one or more articulation cables 410.

Referring back to FIGS. 4A-4C, the second segment 237 may include an actuation cable channel 354. The actuation cable channel 354 may include a first opening at a diametric midpoint of the semi-spherical body portion of the second segment 237 and a second opening at a diametric midpoint of the first portion 350 of the second segment 237.

The actuation cable channel 354 may include an upper taper 359 joined at the first opening that conforms the first opening with a first cylindrical cavity 358 of the body of the second segment 237. The upper taper 359 includes a draft angle $\alpha_3$, which can range between 0° and 45°. The first cylindrical cavity 358 may join a second cylindrical cavity 356 of the body of the second segment 237. The first cylindrical cavity 358 may include a bevel 358a at an interface of the first cylindrical cavity 358 and an upper surface 357 of the second cylindrical cavity 356. A diameter of the first cylindrical cavity 358 may be less than a diameter of the second cylindrical cavity 356.

The second segment 237' may further include at least one cavity slot 360, 360a-b formed in the bottom surface 355 of the first portion 350 of the second segment 237'. The at least one cavity slot 360, 360a-b may include a single continuous cavity slot 360 or may include a first cavity slot 360a and a second cavity slot 360b. The first cavity slot 360a may extend from a first articulation cable channel 353a of the at least one articulation cable channel to a second articulation cable channel 353b of the at least one articulation cable channel.

A first articulation cable 410 may be positioned within the first articulation cable channel 353a, the first cavity slot 360a and the second articulation cable channel 353b. The first articulation cable 410 may be secured to a surface of the first cavity slot 360a. For example, the first articulation cable may be welded to the surface of the first cavity slot 360a, glued to the surface of the first cavity slot 360a and/or press fit within the first cavity slot 360a.

The second cavity slot 360b may extend from a third articulation cable channel 353c of the at least one articulation cable channel to a fourth articulation cable channel 353d of the at least one articulation cable channel. A second articulation cable 410 may be positioned within the third articulation cable channel 353c, the second cavity slot 360b and the fourth articulation cable channel 353d.

The at least one cavity slot 360 may extend about an entire perimeter or circumference of the bottom surface 355 of the first portion 350 or cylindrical body portion of the second segment 237. In this manner, the second opening of the at least one articulation cable channel 353, 353a-d may be partially defined by the at least one cavity slot 360. At least one articulation cable 410 may be positioned within the at least one articulation cable channel 353, 353a-d, and may be secured to a surface of the at least one cavity slot 360.

The segment links 236, 237 may include a material selected from the group consisting of: metal, plastic, a thermoplastic polymer, stainless steel, polyvinyl chloride, a liquid-crystal polymer and polytetrafluoroethylene. The segment links 236, 237 may be rigid. The second segment link 237 may include a material different from that of the first segment link 236.

In some embodiments, a height of the second portions 312, 352 of the segment links 236, 236a-e, 237 may be different such that an angle of articulation between one or more segment links can be restricted to different angles of articulation. For example, a first segment link 236, 237 or a first group of segment links may be restricted to 12° to 15° per segment, and a second segment link 236, 237 or a second group of segment links may be restricted to 8° to 11° per segment.

FIGS. 5A and 5B are perspective views illustrating articulation ranges of the articulating surgical tool illustrated at FIG. 2. The articulation region 235 of the surgical tool 200 is illustrated in varying articulation states 901a-i.

As described above, the articulation region 235 of the tool shaft may include one or more segment links 236, 237. In embodiments including two or more segments links 236, 237, each segment link 236, 237 may be sequentially coupled. In this manner, a plurality of segment links 236, 237 may articulate with respect to one another.

The segment links 236, 237 of the articulation region may be constructed and arranged to restrict an angle of articulation. For example, a bottom surface of a first portion of a first segment link may abut an upper surface of a first portion of a second segment link to restrict an angle of articulation with respect to a center axis of each of the first and second segment links.

In some embodiments, the angle of articulation can be restricted to 12° to 15° per segment 236, 237. For example, referring to the articulation state 901f, a surgical tool 200 including a single segment link 237 may be restricted to a maximum angle of articulation $\alpha_4$ that ranges between 12° to 15°. Referring to the articulation state 901e a surgical tool 200 including two segment links 236a, 237 may be restricted to a maximum angle of articulation $\alpha_5$ that ranges between 24° to 30°. Referring to the articulation state 901d, a surgical tool 200 including three segment links 236a-b, 237 may be restricted to a maximum angle of articulation $\alpha_6$ that ranges between 36° to 45°. Referring to the articulation state 901c, a surgical tool 200 including four segment links 236a-c, 237 may be restricted to a maximum angle of articulation $\alpha_7$ that ranges between 48° to 60°. Referring to the articulation state 901b, a surgical tool 200 including five segment links 236a-d, 237 may be restricted to a maximum angle of articulation $\alpha_8$ that ranges between 60° to 75°. Referring to the articulation state 901a, a surgical tool 200 including six segment links 236a-e, 237 may be restricted to a maximum angle of articulation $\alpha_9$ that ranges between 72° to 90°. Referring to the articulation state 901g, a surgical tool 200 including seven segment links may be restricted to a maximum angle of articulation $\alpha_{10}$ that ranges between 84° to 105°. Referring to the articulation state 901h, a surgical tool 200 including nine segment links may be restricted to a maximum angle of articulation $\alpha_{11}$ that ranges between 108° to 135°. Referring to the articulation state 901i, a surgical tool 200 including twelve segment links may be restricted to a maximum angle of articulation $\alpha_{12}$ that ranges between 144° to 180°. Accordingly, an articulation state of the surgical tool 200 including n segment links may be restricted to a maximum angle of articulation $\alpha$ that ranges between (12*n)° to (15*n)°.

Referring to FIGS. 6A, 6B, 7, 8A-8E and 9, the alternative segment link configurations illustrated therein may be readily incorporated into the articulating surgical tool 200 shown in FIGS. 2 and 3. For example, any one of the articulation regions 235 illustrated in FIGS. 6A, 6B, 7, 8A-8E and 9 may replace the articulation region 235 shown in FIGS. 2 and 3.

FIG. 6A is a side perspective view illustrating an alternative segment link configuration of an articulating surgical tool. As described above, the surgical tool 200 can be configured to include an articulation region 235 having a plurality of segment links 236, 237 having convex body portions 312, 352 (e.g., semi-ellipsoidal body portions, semi-spherical body portions) oriented in a direction facing the functional element 250 as shown in FIG. 6A. The segment links 236, 237 shown in FIG. 6A may be substantially similar to the segment links 236, 237 shown in FIGS. 3 and 4A-4C and are indicated as having like reference characters.

FIG. 6B is a side perspective view illustrating an alternative segment link configuration of an articulating surgical tool, and FIG. 6C is a sectional view of the third segment links illustrated in FIG. 6B. The articulation region 235 of the surgical tool 200 may include a first segment link 237, one or more second segment links 610a-b, and one or more third segment links 611a-b. For example, in the embodiment shown in FIG. 6B, the articulation region 235 includes a first segment link 237, two (2) second segment links 610a-b and two (2) third segment links 611a-b.

The first segment link 237 may be similar to the distal segment link 237 shown in FIGS. 4A-4C, and may be coupled to the functional element 250. However, as described above, the articulation region 235 may be provided at any position between the functional element 250 and the proximal end 215p of the tool shaft 215 (see for example FIG. 2).

At least one second segment link 611a-b may be coupled directly or indirectly to the tool shaft 215, 220. For example, the second segment 611b may be coupled to the second tool shaft 220 via the cable transitioning segment 225, which may distribute multiple cables (e.g., one or more actuating cables 420 and/or one or more articulation cables 410) from the tool shaft 215, 220 to channels 612a-b, 616a-b of the segment links 610a-b, 611a-b, 237.

At least one third segment link 611a-b may be coupled between the first segment link 237 and one of the second segment links 610a-b. For example, in the embodiment shown in FIG. 6B, the third segment link 611a is coupled between the first segment 237 and the second segment link 610a, and the third segment link 611b is coupled between the second segment link 610a and the second segment link 610b.

The second segment link 610a-b may include a body 620 having first and second concave cavities 621a-b formed at opposite end surfaces of the body 620. The first and second concave cavities 621a-b may include semi-ellipsoidal cavities or semi-spherical cavities. In an embodiment having semi-spherical cavities, the semi-spherical cavities may have spherical radii that match spherical radii of semi-spherical body portions of the third segment links 611a-b.

The first concave cavity 621a may join a first taper 613 of the body 620 of the second segment link 610a-b, and the first taper 613 may conform the first concave cavity 621a to a first opening of a cylindrical cavity 614. The second concave cavity 621b may join a second taper 615 of the body 620 of the second segment link 610a-b, and the second taper 615 may conform the second concave cavity 621b to a second opening of the cylindrical cavity 614. In this manner, an actuation cable channel may be formed within the body 620 of the second segment link 610a-b, extending from the first concave cavity 621a to the second concave cavity 621b. In addition, the first and second tapers 613, 615 may prevent pinching of an actuation cable 420 positioned within the actuation cable channel of the second segment link 610a-b during articulation states of the articulation region 235.

The third segment link 611a-b may include a body having a first convex body portion 623a, a second body portion 622, and a third convex body portion 623b. The first and third body portions 623a-b may include semi-ellipsoidal body portions or semi-spherical body portions, and the second body portion 622 may include a cylindrical body portion.

The third segment link 611a-b may include a first taper 617 joined at a first opening in the first convex body portion 623a. The first taper 617 may conform the first opening in the first convex body portion 623a to a cylindrical cavity 618 of the third segment 611a-b. The third segment link 611a-b may include a second taper 619 joined at a second opening in the second convex body portion 623b. The second taper 619 may conform the second opening in the second convex body portion 623b to the cylindrical cavity 618 of the third segment 611a-b. In this manner, an actuation cable channel may be formed within the body of the third segment link 611a-b, extending from the first opening in the first convex body portion 623a to the second opening in the second convex body portion 623b. In addition, the first and second tapers 617, 619 may prevent pinching of an actuation cable 420 positioned within the actuation cable channel of the third segment link 611a-b during articulation states of the articulation region 235.

As described above with reference to the segment links 236, 237 shown in FIGS. 4A-4C, the second and third segment links 610a-b, 611a-b may likewise include at least one articulation cable channel 612a-b, 616a-b. The at least one articulation cable channel 612a-b, 616a-b may include a first opening in a first surface 624, 626 of the bodies of the second and third segment links 610a-b, 611a-b, and a second opening in a second surface 625, 627 of the bodies of the second and third segment links 610a-b, 611a-b. For example, in the embodiments shown at FIG. 6B, the at least one articulation cable channel of the second and third segment links 610a-b, 611a-b may comprise first through fourth articulation cable channels that are spaced 90° apart around the circumference or perimeter of the bodies of the second and third segment links 610a-b, 611a-b. The at least one articulation cable channel may also comprise first through fourth articulation cable channels that are positioned 90° apart from one another along a common radial path relative to a center axis of the second and third segment links 610a-b, 611a-b.

Figure 7:
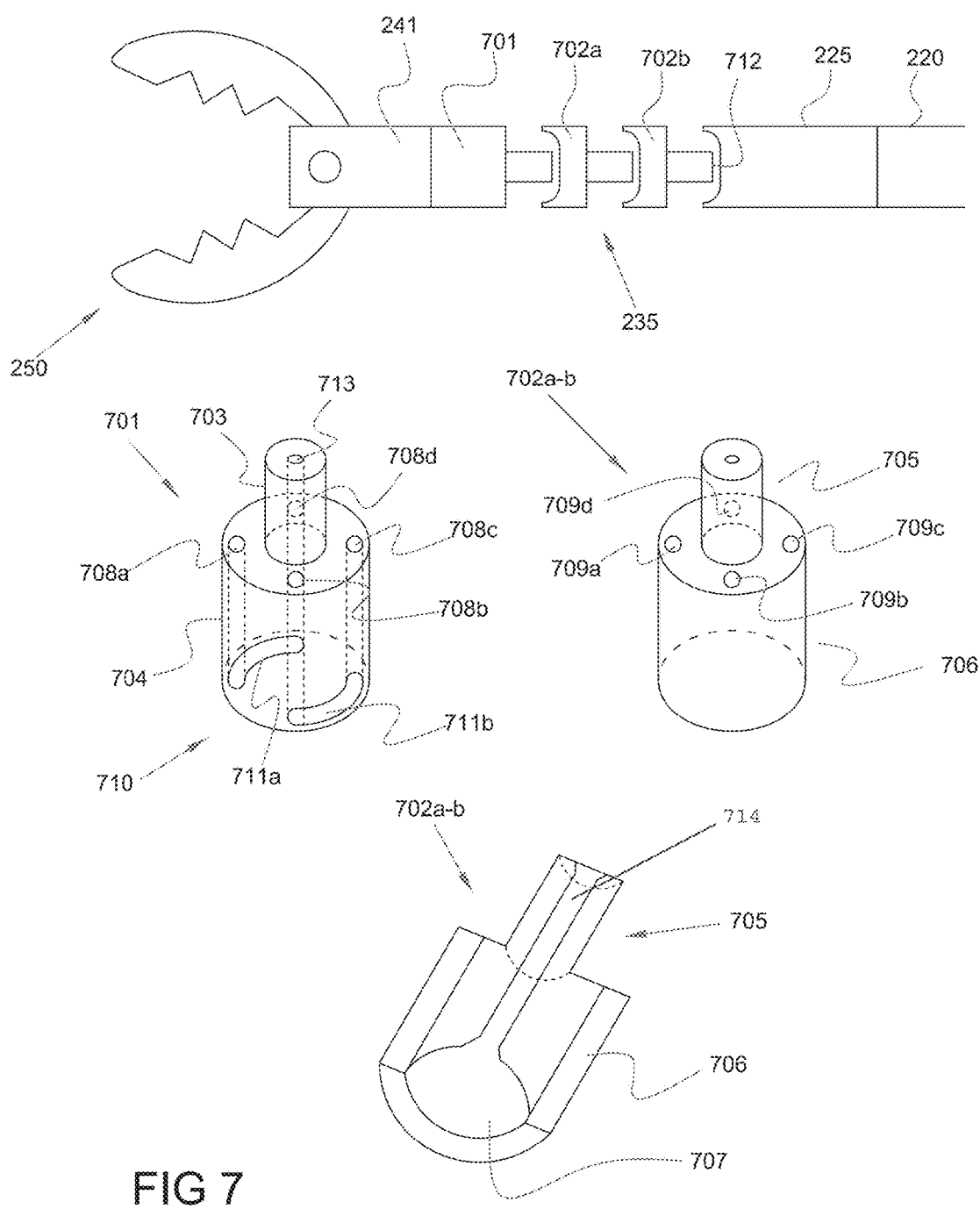
FIG. 7 is a perspective view illustrating an alternative segment link configuration of an articulating surgical tool, in accordance with embodiments of the present inventive concepts.

FIG. 7 is a perspective view illustrating an alternative segment link configuration of an articulating surgical tool. The articulation region 235 of the surgical tool 200 may include a first segment link 701 and one or more second segment links 702a-b. For example, in the embodiment shown in FIG. 7, the articulation region 235 includes a first segment link 701 and two (2) second segment links 702a-b.

The first segment link 701 may include a body 704 and a protrusion 703. The body 704 may include a body having an elliptical cross-section or a cylindrical body, and the protrusion 703 may include an elliptical protrusion or a cylindrical protrusion. For example, in the embodiment shown in FIG. 7, the first segment link 701 is shown having a cylindrical body and a cylindrical protrusion. A diameter of the body 704 may be greater than a diameter of the protrusion 703.

The first segment link 701 may include at least one cavity slot 711a-b formed in a bottom surface 710 of the body 704. The at least one cavity slot 711a-b may be similar to the at least one cavity slot 360, 360a-b formed in the bottom surface 355 of the first portion 350 of the second segment 237 shown in FIG. 4B. The at least one cavity slot may include a single continuous cavity slot (not shown), such as the single continuous cavity slot 360 shown in FIG. 4B or may include a first cavity slot 711a and a second cavity slot 711b as shown in FIG. 7.

The second segment link 702a-b may include a body 706 and a protrusion 705. The body 706 may include a body having an elliptical cross-section or a cylindrical body, and the protrusion 705 may include an elliptical protrusion or a cylindrical protrusion. For example, in the embodiment shown in FIG. 7, the second segment link 702a-b is shown having a cylindrical body and a cylindrical protrusion. A diameter of the body 706 may be greater than a diameter of the protrusion 705.

The second segment link 702a-b may include at least one concave cavity 707. The concave cavity may include a semi-ellipsoidal cavity or a semi-spherical cavity. In this manner, a protrusion 703, 705 of the first and second segment links 701, 702a-b may mate with a concave cavity 707 of another second segment link 702a-b. For example, in the embodiment shown in FIG. 7, the protrusion 703 of the first segment link 701 is shown mated with the concave cavity 707 of the second segment link 702a, and the protrusion 705 of the second segment link 702a is shown mated with the concave cavity 707 of the second segment link 702b. In this example, the cable transitioning segment 235 includes a concave cavity 712, which is shown mated with a protrusion 705 of the second segment link 702b.

As described above with reference to the segment links 236, 237 shown in FIGS. 4A-4C, the first and second segment links 701, 702a-b may likewise include at least one articulation cable channel 708a-d, 709a-d. The at least one articulation cable channel 708a-d, 709a-d may include a first opening in a first surface of the bodies 704, 706 of the first and second segment links 701, 702a-b, and a second opening in a bottom surface of the bodies 704, 706 of the first and second segment links 701, 702a-b. For example, in the embodiments shown at FIG. 7, the at least one articulation cable channel of the first and second segment links 701, 702a-b may comprise first through fourth articulation cable channels 708a-d, 709a-d that are spaced 90° apart around the circumference or perimeter of the bodies 704, 706 of the first and second segment links 701, 702a-b. The at least one articulation cable channel may also comprise first through fourth articulation cable channels 708a-d, 709a-d that are positioned 90° apart from one another along a common radial path relative to a center axis of the first and second segment links 701, 702a-b.

The first and second segment links 701, 702a-b may include actuation cable channels 713, 714. The actuation cable channels 713, 714 may include a first opening at a diametric midpoint of the protrusions 703, 705 and a second opening at a diametric midpoint of the bottom surfaces of the bodies 704, 706. Although not shown, the first and second openings may join first and second tapers that conform the first and second openings to a cylindrical cavity so as to form a channel. As described above, the tapers may prevent pinching of an actuation cable 420 positioned within the actuation cable channels 713, 714 of the segment links 701, 702a-b during articulation states of the articulation region 235.

Figure 8A:
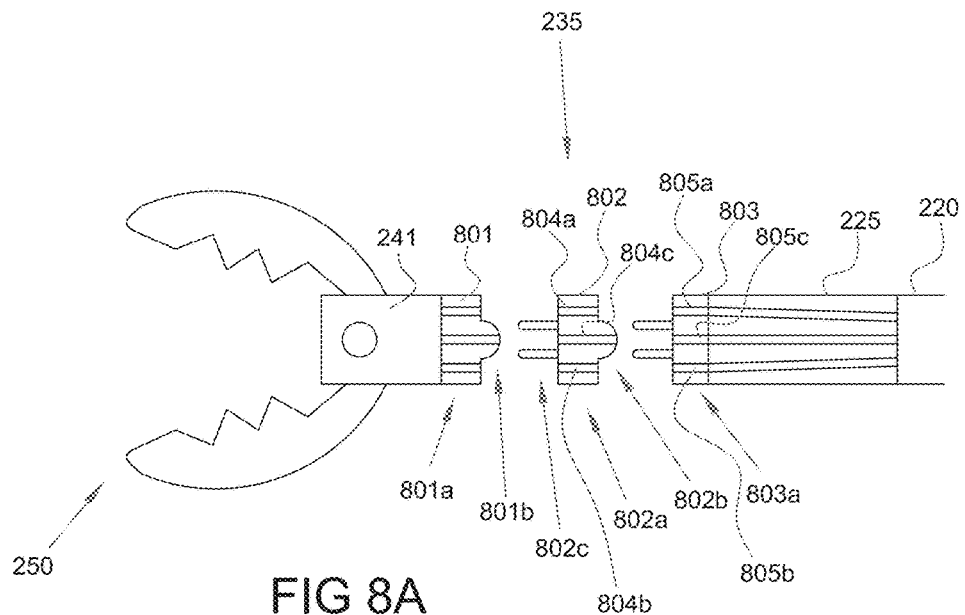
FIG. 8A is a perspective view illustrating an alternative segment link configuration of an articulating surgical tool, in accordance with embodiments of the present inventive concepts.

FIG. 8A is a perspective view illustrating an alternative segment link configuration of an articulating surgical tool. The articulation region 235 of the surgical tool may include a first segment link 801, one or more second segment links 802, and a third segment link 803.

The first segment link 801 may include a body having a first body portion 801a and a second body portion 801b. The first body portion 801a may include a body portion having an elliptical cross-section or a cylindrical body portion, and the second body portion 801b may include a convex body portion, a semi-ellipsoidal body portion or a semi-spherical body portion. The first segment link may be similar to the distal segment link 237 shown in FIGS. 4A-4C.

The second segment links 802 may include a first body portion 802a, a second body portion 802b, and a plurality of protruding posts 802c extending from a surface of the first body portion 802a. The first body portion 802a may include a body portion having an elliptical cross-section or a cylindrical body portion, and the second body portion 802b may include a convex body portion, a semi-ellipsoidal body portion or a semi-spherical body portion. The posts 802c may include cylindrically shaped posts, and may have rounded or beveled top surfaces.

The third segment link 803 may include a first body portion 803a and a plurality of protruding posts 802c extending from a surface of the third body portion 803a. The posts 803b may include cylindrically shaped posts, and may have rounded or beveled top surfaces.

The second body portion 801b of the first segment 801 may mate with the plurality of posts 802c of the second segment 802, and the second body portion 802b of the second segment link 802 may mate with the plurality of posts 803b of the third segment 803. In this manner, friction may be reduced at the interface between the second body portion 801b of the first segment link 801 and the posts 802c of the second segment link 802, and the interface between the second body portion 802b of the second segment link 802 and the posts 803b of the third segment link 803.

As described above with reference to the segment links 236, 237 shown in FIGS. 4A-4C, the second and third segment links 802, 803 may likewise include at least one articulation cable channel 804a-b, 805a-b. For example, in the embodiments shown at FIG. 8A, the at least one articulation cable channel of the second and third segment links 802, 803 may comprise first through fourth articulation cable channels that are spaced 90° apart around the circumference or perimeter of the bodies 802a, 803a of the second and third segment links 802, 803. The at least one articulation cable channel may also comprise first through fourth articulation cable channels that are positioned 90° apart from one another along a common radial path relative to a center axis of the second and third segment links 802, 803.

The second and third segment links 802, 803 may include actuation cable channels 804c, 805c. The actuation cable channels 804c, 805c may be positioned at a diametric midpoint of the second and third segment links 802, 803.

FIGS. 8B-8E illustrate alternative post configurations in accordance with the alternative segment link configuration shown in FIG. 8A.

Figures 8B, 8C, 8D, 8E:
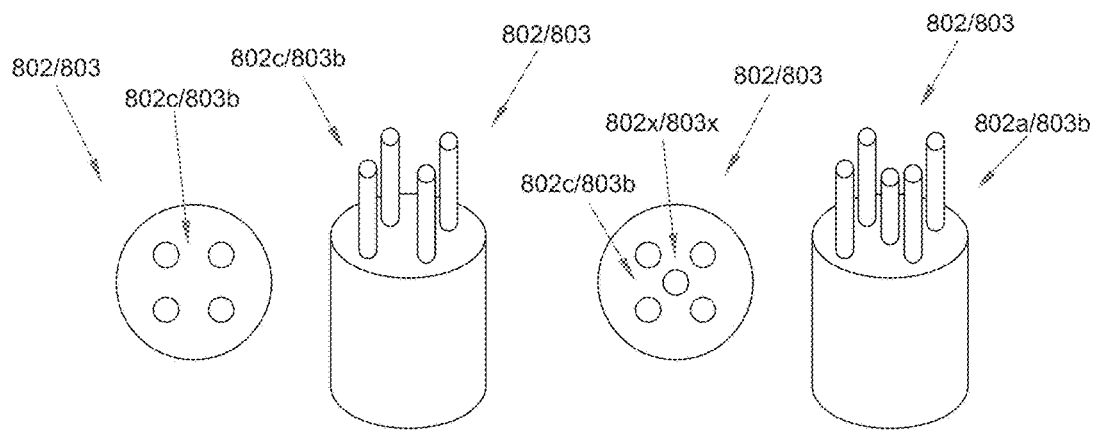
FIG. 8B is a perspective view of a segment link, in accordance with embodiments of the present inventive concepts.
FIG. 8C is a top view of the segment link illustrated in FIG. 8B, in accordance with embodiments of the present inventive concepts.
FIG. 8D is a perspective view of a segment link, in accordance with embodiments of the present inventive concepts.
FIG. 8E is a top view of the segment link illustrated in FIG. 8D, in accordance with embodiments of the present inventive concepts.

FIG. 8B is a perspective view of a segment link, and FIG. 8C is a top view of the segment link illustrated in FIG. 8B. As described above, the second and third segment links 802, 803 may include a plurality of posts 802c, 803b. The plurality of posts 802c, 803b may be arranged along a common radial path relative to a center axis of the second and third segment links 802, 803, and may be spaced apart by a common distance. For example, in the embodiment shown in FIGS. 8B and 8C, the plurality of posts 802c, 803b include first through forth posts. The plurality of posts 802c, 803b may have a common height.

FIG. 8D is a perspective view of a segment link, and FIG. 8E is a top view of the segment link illustrated in FIG. 8D. As described above, the second and third segment links 802, 803 may include a plurality of posts 802c, 803b. The plurality of posts 802c, 803b may be arranged along a common radial path relative to a center post 802x, 803x of the second and third segment links 802, 803, and may be spaced apart by a common distance. For example, in the embodiment shown in FIGS. 8D and 8E, the plurality of posts 802c, 803b include first through fourth posts. The first through fourth posts are arranged along a common radial path relative to the center post 802x, 803x. In this exemplary configuration, the plurality of posts 802c, 803b arranged about the center posts 802x, 803x and may each have a first height greater than a second height of the center post 802x, 803x.

Figure 9:
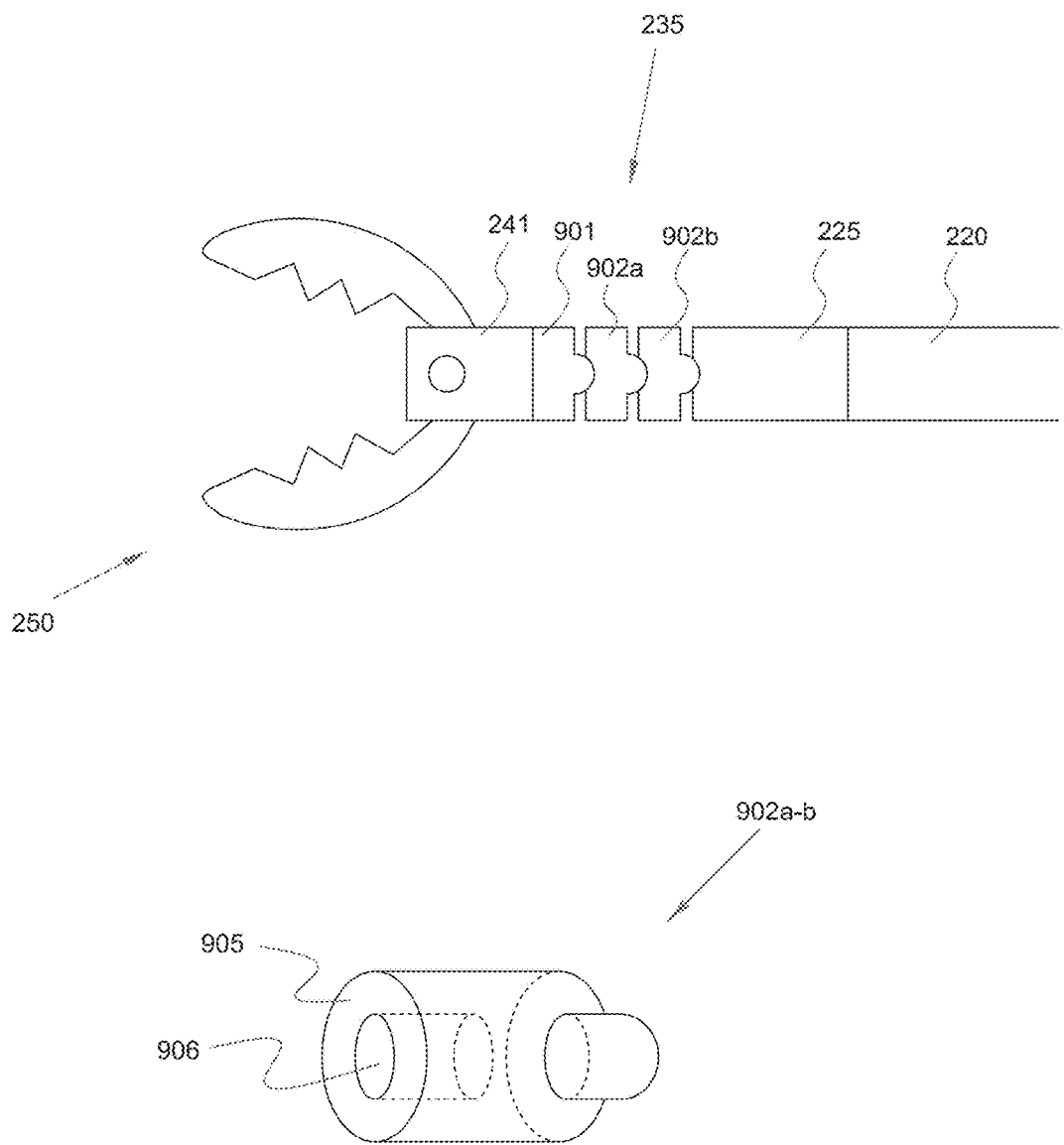
FIG. 9 is a perspective view illustrating an alternative segment link configuration of an articulating surgical tool, in accordance with embodiments of the present inventive concepts.

FIG. 9 is a perspective view illustrating alternative segment links of an articulating surgical tool. The articulation region 235 of the surgical tool may include a first segment link 901 and one or more second segment links 902a-b.

The first segment link 901 may be similar to the distal segment link 237 shown in FIGS. 4A-4C, and the second segment links 902a-b may be similar to the first segment link 236 shown in FIGS. 4A-4C. However, instead of including a concave cavity 316 as shown in FIGS. 4A-4C, the second segment links 902a-b may include an elliptical or circular opening 906 formed in the bottom surface 905 of the second segment links 902a-b. The opening 906 may have a diameter less than twice the spherical radius of the convex body portions of the first and second segments 901, 902a-b so that when mated, the convex body portions of the first and second segment 901, 902a-b partially protrude within the opening 906.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following claims.

What is claimed is:

1. A system for performing a medical procedure comprising:
   an articulation probe including inner and outer sleeves, the inner sleeve at least partially surrounded by the outer sleeve, each of the inner and outer sleeves comprising a plurality of segment links, the articulating probe further comprising a locking mechanism configured in one of a locked or unlocked mode and a port extending through the segment links of the inner and outer sleeves; and
   a surgical tool that articulates independently of and relative to the segment links of the inner and outer sleeves of the articulating probe, the surgical tool including a tool shaft and a functional element positioned at a distal end of the tool shaft, the tool shaft having an articulating region,
   wherein the tool shaft includes a plurality of segment links, wherein each of the plurality of segment links of the tool shaft includes a plurality of articulation cable channels,
   wherein the surgical tool further comprises a plurality of articulation cables, each of which is positioned in a respective one of the plurality of articulation cable channels,
   wherein the segment links of the inner and outer sleeves of the articulating probe and the segment links of the tool shaft of the surgical tool are independently controllable,
   wherein the locking mechanism is constructed and arranged to secure the tool shaft including the articulation cables, cable channels, and tool shaft segment links in the port of the segment links of the inner and outer sleeves of the articulating probe in the locked mode,
   wherein the locking mechanism is constructed and arranged to allow the tool shaft to movably pass through the articulating probe in the unlocked mode,
   wherein the articulating probe and the surgical tool are independently controllable in the unlocked mode of the locking mechanism, and
   wherein the locking mechanism comprises at least one of a pneumatic lock, a pneumatic solenoid, a pneumatic expandable pouch, a hydraulic lock, a hydraulic solenoid, a hydraulic expandable pouch, an electrically activated lock, an electrically activated solenoid, or an electrically activated piezoelectric actuator.

2. The system of claim 1, wherein each segment link of the plurality of segment links is sequentially coupled to another segment link of the plurality of segment links.

3. The system of claim 1, wherein each segment link of the plurality of segment links is constructed and arranged to provide 12° to 15° of articulation between the functional element and a working surface of the articulating probe.

4. The system of claim 1, wherein each segment link of the plurality of segment links is constructed and arranged to provide 12° to 15° of articulation between the functional element and a longitudinal axis of a cable transitioning segment of the tool shaft.

5. The system of claim 1, wherein each segment link of the plurality of segment links is constructed and arranged to provide 12° to 15° of articulation between the functional element and an axis of extension of the tool shaft.

6. The system of claim 1, wherein the surgical tool is positioned in a working channel, side port, or guide hole of the segment links of the inner and outer sleeves of the articulating probe.

7. The system of claim 1, wherein the surgical tool further comprises:
 a connection link coupled to a segment link at the distal end;
 an actuator piston positioned in an inner cavity of the connection link; and
 an actuator cable extending through the plurality of segment links to engage the actuator piston in the connection link.

8. The system of claim 7, wherein the plurality of articulation cables is secured to the actuator piston.

9. The system of claim 7, wherein a segment link of the plurality of segment links of the tool shaft comprises a cavity slot for receiving an articulation cable from one of the plurality of articulation cable channels and for directing the articulation cable to another of the plurality of articulation cable channels.

10. The system of claim 1, wherein the plurality of segment links articulate with respect to one another.

11. The system of claim 10, wherein a bottom surface of a first portion of a first segment link of the plurality of segment links abuts an upper surface of a first portion of a second segment link of the plurality of segment links to restrict an angle of articulation with respect to a common center axis extending through a center of each of the first and second segment links, and wherein the first and second segment links articulate relative to each other, wherein each of the bottom surface of the first portion of the first segment link and the upper surface of the first portion of the second segment link extends circumferentially and peripherally about the common center axis such that any region of the bottom surface of the first portion of the first segment link either directly abuts a corresponding region of the upper surface of a first portion of a second segment link or is separate from the corresponding region of the upper surface of a first portion of a second segment link, depending on the angle of articulation with respect to the common center axis.

12. The system of claim 11, wherein the angle of articulation is restricted to 12° to 15°.

13. The system of claim 11, wherein the first portion of the first segment link includes a cylindrical body portion and the first portion of the second segment link includes a cylindrical body portion.

* * * * *